United States Patent [19]
Norling et al.

[11] Patent Number: 5,958,458
[45] Date of Patent: Sep. 28, 1999

[54] PHARMACEUTICAL MULTIPLE UNIT PARTICULATE FORMULATION IN THE FORM OF COATED CORES

[75] Inventors: Tomas Norling, Lyngby; Lone Norgaard Jensen, Soborg; Jens Hansen, Allerod, all of Denmark

[73] Assignee: Dumex-Alpharma A/S, Copenhagen, Denmark

[21] Appl. No.: 08/509,107

[22] Filed: Aug. 1, 1995

Related U.S. Application Data

[63] Continuation-in-part of application No. 08/268,037, Jun. 29, 1994.

[30]    Foreign Application Priority Data

Jun. 15, 1994 [DK] Denmark ................................ 0695/94

[51] Int. Cl.⁶ .............................. A61K 9/16; A61K 47/02
[52] U.S. Cl. ........................ 424/490; 424/489; 424/468; 424/469; 424/466; 514/951
[58] Field of Search ........................... 424/422, 458–462, 424/469–470, 489–502, 421, 687, 466, 471; 514/951, 952

[56]                References Cited

U.S. PATENT DOCUMENTS

| | | |
|---|---|---|
| 4,064,230 | 12/1977 | Gordon et al. . |
| 4,096,246 | 6/1978 | Oystese . |
| 4,395,491 | 7/1983 | Hohl et al. . |
| 4,713,245 | 12/1987 | Ando et al. . |
| 4,844,734 | 7/1989 | Iwasaki et al. . |
| 5,055,307 | 10/1991 | Tsuru et al. . |
| 5,158,777 | 10/1992 | Abramowitz et al. . |
| 5,324,649 | 6/1994 | Arnold et al. . |
| 5,549,915 | 8/1996 | Volkonsky et al. . |

FOREIGN PATENT DOCUMENTS

| | | |
|---|---|---|
| 0 193 984 A2 | 9/1986 | European Pat. Off. . |
| 0 537 070 A1 | 4/1993 | European Pat. Off. . |
| 0 608 850 A1 | 8/1994 | European Pat. Off. . |
| 24 56 463 C2 | 8/1976 | Germany . |
| 57-053232 | 3/1982 | Japan . |
| 58-166926 | 10/1983 | Japan . |
| 59-093013 | 5/1984 | Japan . |
| 61-047410 | 3/1986 | Japan . |
| 3181410 | 8/1991 | Japan . |
| 4013614 | 1/1992 | Japan . |
| 70025919 | of 1993 | Japan . |
| 1 543 360 | 4/1979 | United Kingdom . |
| 2 190 287 | 11/1987 | United Kingdom . |
| WO 93/07859 | 4/1993 | WIPO . |

*Primary Examiner*—Edward J. Webman
*Attorney, Agent, or Firm*—Watov & Kipnes, P.C.

[57]                ABSTRACT

A pharmaceutical multiple unit particulate formulation in the form of coated cores which includes a pharmaceutically acceptable carrier selected from calcium carbonate, calcium silicate, calcium magnesium silicate, calcium phosphate, kaolin, sodium hydrogen carbonate, sodium sulfate, barium carbonate, barium sulfate, magnesium sulfate, magnesium carbonate, and activated carbon, and an active substance in a layer on the outer surface of the cores.

20 Claims, 8 Drawing Sheets

PHARMACEUTICAL MULTIPLE UNIT PARTICULATE FORMULATION IN THE FORM OF COATED CORES

This is a continuation-in-part application of U.S. patent application Ser. No. 08/268,037 filed Jun. 29, 1994, which claims the priority of DK 0695/94 filed Jun. 15, 1994.

FIELD OF THE INVENTION

The present invention relates to a pharmaceutical multiple unit particulate formulation in the form of cores such as, e.g., coated cores, and to a process for the preparation thereof.

The invention relates also to drug delivery systems, e.g. in the form of a solid dosage form or a liquid formulation comprising a pharmaceutical formulation according to the invention.

BACKGROUND OF THE INVENTION

During the last two decades research within the pharmaceutical field has focused on developing novel drug delivery systems.

However, the utility of the known drug delivery systems in the form of pharmaceutical formulations is generally limited either to a certain administration route such as, e.g., the oral route, or, alternatively, to a certain physical state of the formulation, such as, e.g., the solid state, semi-solid state, liquid state etc. A marked and advantageous improvement within the pharmaceutical formulation field would therefore be to identify and develop a general principle for formulation of pharmaceutical formulations which may be employed in drug delivery systems without regard to the administration route and/or the physical state of the drug delivery systems.

DESCRIPTION OF THE INVENTION

Figure 1:
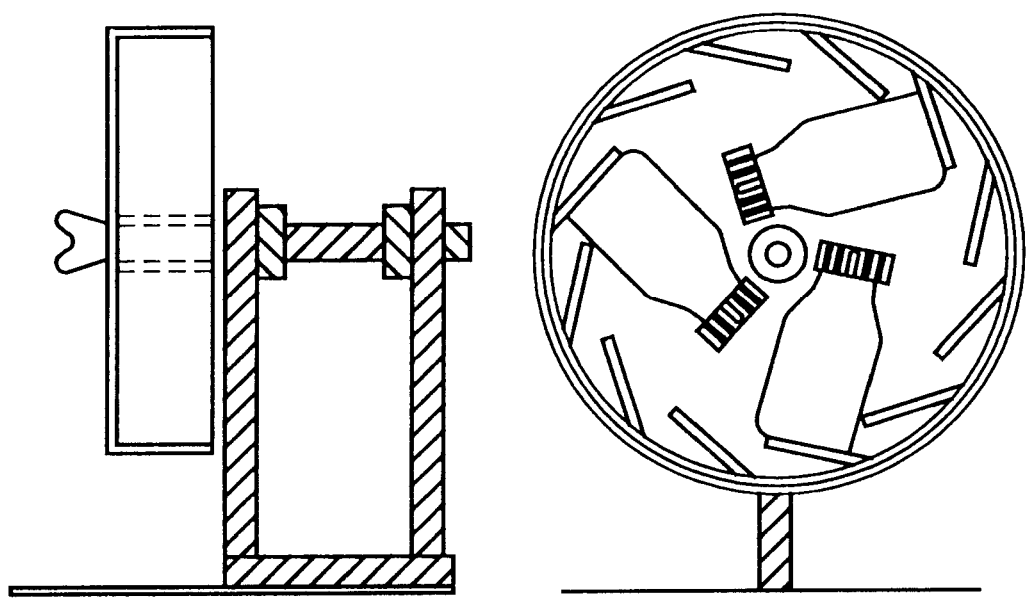
FIG. 1 shows a schematic drawing of the Erweka apparatus employed in the friability test (for further details, see under the heading "Apparatus and Methods")

As will be apparent from the above, there is still a need for developing and preparing pharmaceutical formulations which may be employed in the preparation of different types of drug delivery systems, such as, e.g., drug delivery systems in the form of solid dosage forms as well as in the form of liquid formulations.

The present invention meets this need by providing a pharmaceutical particulate formulation in the form of a multiple unit formulation. The formulation comprises individual units in the form of cores, such as, e.g., coated cores comprising i) a pharmaceutically acceptable inert carrier which is present in the core in a first concentration of at least about 20% w/w calculated on the total weight of the core, and which is selected from the group consisting of calcium carbonate, calcium silicate, calcium magnesium silicate, calcium phosphate, kaolin, sodium hydrogen carbonate, sodium sulfate, barium carbonate, barium sulfate, magnesium sulfate, magnesium carbonate, and activated carbon, and ii) an active substance, the pharmaceutically acceptable inert carrier being such a material which—when formulated into uncoated cores containing the pharmaceutically acceptable inert carrier optionally in combination with a binder and with a second concentration of the inert carrier of at least 80% w/w calculated on the total weight of the uncoated core—has a friability (weight loss in % w/w) of at the most about 20%, when tested as described herein, and the cores have a flow angle—when tested according to method A described herein using a diameter of the disc outlet of 9 mm—of at the most 30°.

A pharmaceutical formulation according to the present invention is based on a novel principle allowing preparation of cores such as, e.g., cores in the form of pellets, i.e. substantially spheric particles which have such a mechanical strength (expressed in terms of friability, see above) that the cores are sufficiently robust to substantially remain intact after having been subjected to coating by standard pharmaceutical procedures well known by a person skilled in the art such as, e.g., a coating process involving a fluidized bed process.

A sufficient robustness of the cores is obtained by employing a pharmaceutically acceptable inert carrier which when it itself is formulated into uncoated cores shows well-defined properties with respect to mechanical strength/robustness (see below) and, furthermore, by employing such a suitable inert carrier material in a pharmaceutical formulation according to the invention in a concentration of at least 20% w/w such as, e.g., at least about 30% w/w, 40% w/w, 50% w/w, 60% w/w, 70% w/w, 75% w/w, 80% w/w, or 85% w/w calculated on the total weight of the cores. In a currently preferred embodiment, the concentration of the inert carrier in the cores is at least about 75%, and in some cases the concentration may be even higher. The concentration of the inert carrier in the cores depends mainly on the following two factors: i) the objective of obtaining sufficiently robust cores (in general, the robustness increases as the concentration of the inert carrier in the cores increases), and ii) the loading of active substance which generally is determined by the required dosage of the active drug substance in question, the disease to be treated, the age and weight of the animal, including mammals such as, e.g., a human to be treated, and the duration of the effect of the active substance.

As mentioned above, the cores contained in a formulation according to the present invention comprise a pharmaceutically acceptable inert carrier and an active substance.

In the present context, the term "pharmaceutically acceptable inert carrier" designates a substance which is generally accepted for use as a pharmaceutical excipient, which is safe, i.e. is regarded as a non-toxic substance, and which has such mechanical properties that when the inert carrier in itself is in the form of uncoated cores which substantially are based on the inert carrier, then the thus obtained cores in themselves have a sufficient mechanical strength expressed by means of friability. Such cores which also may be denoted "inert cores" are uncoated and do not contain any active substance (as defined herein). However, the inert cores may contain the inert carrier optionally in combination with one or more pharmaceutically acceptable excipient such as, e.g., a binder. When testing the mechanical strength of the inert cores by means of measuring the friability of the inert cores, the concentration of the inert carrier in the uncoated inert cores should be at least about 80% w/w such as, e.g., at least about 85%, at least about 90% w/w or about 95% w/w, calculated on the total weight of the uncoated core. These minimum requirements with respect to concentration of the inert carrier in the inert cores are made in order to ensure that the robustness of the cores expressed by means of friability is in fact an effect which primarily is due to the presence of the inert carrier and not an effect which is obtained as a consequence of the presence of another material. It is appreciated that the other ingredients present in the inert core, if any, may contribute to the resulting friability of the inert cores (either by lowering or raising the friability) but this possible contributing effect should not dominate the effect from the inert carrier.

As mentioned above, when testing the robustness of the uncoated inert cores comprising the inert carrier optionally in combination with a pharmaceutically acceptable excipient such as, e.g., a binder, the friability (weight loss in % w/w) of the inert cores should be at the most about 20% w/w such as, e.g, at the most about 15%, at the most about 14% or about 13%, or even lower, when tested as described in the experimental section herein.

The cores employed in a pharmaceutical formulation according to the invention as well as the inert cores described above may be prepared by techniques well known in the art such as, e.g., rotary bed (e.g. in a Glatt GFCG Rotor Insert Type GRG-1), extrusion, granulation and treatment in a intensive mixer, or spray drying. Optionally, one or more pharmaceutically acceptable excipients are added when the cores are prepared. In order to secure a relatively small particle size of the cores, however, the cores preferably are prepared by a spray drying process whereby cores of reproducible sizes and size distribution are obtained and, furthermore, a spray drying process is a relatively simple, dustless and economic one-step method. Although spray drying has proved to be an advantageous method within the pharmaceutical industry for the preparation of powders, pellets, granules etc. resulting in spray dried materials having a spherical geometric form and a narrow size distribution, the product obtained from such a process is normally regarded as unsuitable for coating purposes. The reason is that spray dried powders are usually of hollow nature. The hollow nature of spray-dried powders has made it almost impossible to coat spray-dried particles due to the fact that such hollow particles do not have sufficient robustness or mechanical strength to withstand the relatively strong mechanical action which is applied during a coating process. When tried, the result is particles having buds and/or pores emerging on the surface or even ruptured particles (Ting, T.-Y., et al.: Pharm. Res. 1992, 9 (10), 1330–1335). In support of this observation it can be mentioned that spray-drying has found widespread applications in the pharmaceutical field, see, e.g., Broadhead, J., et al.: Drug Develop. Ind. Pharm. 1992, 18 (11&12), 1169–1206, but to the best of our knowledge, the further processing of spray-dried powder into, e.g., coated cores has not been an important issue. The present inventors have now found that by use of certain inert carrier material as basic material within the cores it is possible even after employment of a spray drying method to coat the cores without significant rupture or destruction of the cores. The thus obtained spherical cores are solid and relatively compact and, furthermore, they have a relatively smooth surface which indicate their ability to being provided with a coating. Furthermore, the general characteristics of spray dried powders are obtained such as, e.g. a narrow size distribution, and particles having a relatively small size etc. These characteristics are especially important in relation to development of drug delivery systems for administration of an active substance to e.g. the nasal cavity and the gastrointestinal tract (when the formulation is in the form of a suspension) etc. It is believed that a formulation according to the invention after oral intake will disintegrate in the gastro-intestinal tract into particles (individual units) which have such a small size that the transit time through the gastro-intestinal tract substantially is the same as the transit time for a liquid such as water (i.e. about 4–6 hours). Therefore, a formulation according to the invention is believed to be a suitable drug delivery system also for active substances which advantageously should exert their effects several hours after intake such as, e.g., during sleep or in the morning after sleep (e.g. active substances against morning stiffness and certain cardiac diseases). Furthermore, without any essential rupture of the coating on the cores, a particulate formulation according to the invention may be compressed into multiple unit tablets (cf. the examples herein) which easily may be divided into two or more dosages (due to the observation that the individual units are so small).

In the present context the term "drug delivery system" denotes a pharmaceutical formulation (a pharmaceutical composition or a dosage form) which upon administration presents the active substance to the body of a human or an animal. Thus, the term "drug delivery system" embraces plain pharmaceutical formulations such as, e.g., powders, tablets etc. as well as more sophisticated formulations such as sprays, plasters, devices etc.

As mentioned in the introductory part, an objective of the present invention is to develop a formulation principle which has a widespread applicability e.g. independendly of administration route and/or delivery system. However, in many types of delivery systems wherein solid, i.e. undissolved, particles are included, the usefulness of such a delivery system is dependent of a very small particle size; if the particle size is too high, e.g., in a liquid dispersion for oral intake, it will lead to inconveniences for the patient who swallows the dispersion which in turn leads to non-compliance. The same applies for delivery systems intended for nasal administration where the requirement to particle size is very strict as the size is responsible for whether the active substance will reach the correct site in the organism. Therefore, at least 50% w/w of the cores before coating should have a particle size within a range of about 90–225 $\mu$m such as, e.g., within a range of about 100–225 $\mu$m, when tested as described in the experimental section herein. At present it is preferred that at least about 60% w/w such as, e.g. at least about 70% w/w, about 80% w/w or about 90% w/w of the cores before coating have a particle size within the range of about 90–225 $\mu$m such as, e.g., within the range of about 100–225 $\mu$m.

The mean particle size (i.e. the size of at least 50% w/w of the cores before coating) should be at the most about 250 µm such as, e.g., at the most about 200 µm, at the most about 180 µm or at the most about 170 µm, when tested as described herein. Apart from the above-mentioned requirements to particle size, the cores should not be too small; preferably at the most 10% w/w of the cores should have a particle size below about 20 µm.

Examples of pharmaceutically acceptable inert carriers for use in formulations according to the invention are, e.g., calcium carbonate, calcium silicate, calcium magnesium silicate, calcium phosphate, kaolin, sodium hydrogen carbonate, sodium sulfate, barium carbonate, barium sulfate, magnesium sulfate, magnesium carbonate, and activated carbon.

The pharmaceutically acceptable inert carriers for use in formulations according to the invention may be water soluble or water insoluble. Pharmaceutically acceptable inert carriers which are insoluble in water are especially relevant in those cases where the cores comprising the inert carrier are subjected to further processes in which an aqueous medium is involved such as, e.g., a coating process employing an aqueous coating composition. On the other hand, in those cases where further processing of the cores takes place without involvement of aqueous media, a higher water solubility of the inert carrier for use in formulations according to the invention may be accepted.

Furthermore, the present inventors have found that the preparation of cores having the desired relatively small particle size advantageously takes place when the inert carrier itself has a small particle size. Thus, at the most 80% w/w of the inert carrier particles may have a particle size of at the most 30 µm, or, alternatively, at the most 85% w/w of the inert carrier particles may have a particle size of at the most 10 µm.

When a spray-drying process is employed in the preparation of the cores for use according to the invention, a variety of parameters may be changed and optimized in order to obtain cores having e.g. a suitable particle size, a suitable form, and a suitable density. The density of the inert carrier particles is only one factor among many which may influence the particle form of the final cores. The present inventors have found that it is possible to avoid the formation of hollow spheres after a spray-drying process when the inert carrier has a bulk density in a range of about 0.1–1.0 g/cm$^3$.

A currently preferred pharmaceutically acceptable inert carrier is calcium carbonate, especially calcium carbonate corresponding to calcium carbonate Microstevns from Faxe Kalk, Denmark wherein at least about 90% w/w of the particles have a size of at the most 20 µm, a density of 2.7 g/cm$^3$ and a bulk density of about 0.75 g/cm$^3$ (according to the supplier). Other calcium carbonate qualities may also prove to be suitable such as, e.g., calcium carbonate from Nomeco, Denmark having a bulk density of about 0.25 g/cm$^3$.

As mentioned above, a coating of cores prepared by spray-drying is generally regarded as a difficult task because the cores are substantially hollow. The cores for use in a pharmaceutical particulate formulation according to the invention should therefore not be hollow and/or the bulk density should be at least about 0.25 g/cm$^3$ such as, e.g., at least about 0.4 g/cm$^3$, about 0.5 g/cm$^3$ or about 0.6 g/cm$^3$.

Pellets comprising calcium carbonate are known from the patent literature, see e.g. DK 77/04827 and DK 77/04402. DK 77/04827 related to feed compositions of nitrovin. The composition is in form of pills comprising calcium carbonate, i.e. the composition is not a multiple-unit formulation as a formulation according to the present invention. DK 77/04402 relates to zink-bacitracin compositions for use as animal feed compositions. The compositions comprises particles of zink-bacitracin in admixture with calcium carbonate but are not described as multiple-unit compositions.

Active Substance

Apart from the pharmaceutically acceptable inert carrier, the cores comprise an active substance.

In the present context the term "active substance" is intended to mean any biologically or pharmacologically active substance or antigen-comprising material; the term includes drug substances which have utility in the treatment or prevention of diseases or disorders affecting animals or humans, or in the regulation of any animal or human physiological condition and it also includes any biologically active compound or composition which, when administered in an effective amount, has an effect on living cells or organisms.

The active substances which can be used according to the invention may be selected without limitation among those belonging to the following groups:

analgesic drugs such as, e.g., buprenorphine, codeine, fentanyl, morphine, hydromorphone, and the like;

anti-inflammatory drugs such as, e.g., ibuprofen, indomethacin, naproxen, diclofenac, tolfenamic acid, piroxicam, and the like;

tranquilizers such as, e.g., diazepam, droperiodol, fluspirilene, haloperidol, lorazepam, and the like;

cardiac glycosides such as, e.g., digoxin, ouabain, and the like;

narcotic antagonists such as, e.g., naloxone, nalorphine, and the like;

antiparkinsonism agents such as, e.g., bromocriptine, biperidin, benzhexol, benztropine, and the like;

antidepressants such as, e.g., imipramine, nortriptyline, pritiptylene, and the like;

antineoplastic agents and immunosuppressants such as, e.g., bleomycin, cyclosporin A, fluorouracil, mercaptopurine, methotrexate, mitomycin, and the like;

antiviral agents such as, e.g., idoxuridine, acyclovir, interferons, vidarabin, and the like;

antibiotic agents such as, e.g., clindamycin, erythromycin, fusidic acid, gentamicin, and the like;

antifungal agents such as, e.g., miconazole, ketoconazole, clotrimazole, amphotericin B, nystatin, and the like;

antimicrobial agents such as, e.g., metronidazole, tetracyclines, and the like;

appetite suppressants such as, e.g., fenfluramine, mazindol, phentermin, and the like;

antiemetics such as, e.g., metoclopramide, droperidol, haloperidol, promethazine, and the like;

antihistamines such as, e.g., chlorpheniramine, chlorpheniramine maleate,terfenadine, triprolidine, and the like;

antimigraine agents such as, e.g., dihydroergotamine, ergotamine, pizotyline, and the like;

coronary, cerebral or peripheral vasodilators such as, e.g., nifedipine, diltiazem, and the like;

antianginals such as, e.g., glyceryl nitrate, isosorbide dinitrate, molsidomine, verapamil, and the like;

calcium channel blockers such as, e.g., verapamil, nifedipine, diltiazem, nicardipine, and the like;

hormonal agents such as, e.g., estradiol, estron, estriol, polyestradiol, polyestriol, dienestrol, diethylstilbestrol, progesterone, dihyroergosterone, cyproterone, danazol, testosterone, and the like;

contraceptive agents such as, e.g., ethinyl estradiol, lynestrenol, etynodiol, norethisterone, mestranol, norgestrel, levonorgestrel, desogestrel, medroxyprogesterone, and the like;

antithrombotic agents such as, e.g., heparin, warfain, and the like;

diuretics such as, e.g., hydrochlorothiazide, flunarizine, minoxidil, and the like;

antihypertensive agents such as, e.g., propanolol, metoprolol such as metoprolol tartrate or metoprolol succinate, clonidine, pindolol, and the like;

chemical dependency drugs such as, e.g., nicotine, methadone, and the like;

local anaestehetics such as, e.g., lidocaine, prilocaine, benzocaine, and the like;

corticosteroids such as, e.g., beclomethasone, betamethasone, clobetasol, desonide, desoxymethasone, dexamethasone, diflucortolone, flumethasone, fluocinolone acetonide, fluocinonide, hydrocortisone, methylprednisolone, triamcinolone acetonide, budesonide, halcinonide, and the like;

dermatological agents such as, e.g., nitrofurantoin, dithranol, clioquinol, hydroxyquinoline, isotretionin, methoxsalen, methotrexate, tretionin, trioxsalen, salicylic acid, penicillamine, and the like;

vitamins and the like;

ophthalmic agents such as, e.g., pilocarpin, ephinefrin, timolol, atrophin, and the like;

Other specific examples of active ingredients for use according to the invention are steroids such as, e.g., estradiol, progesterone, norethindrone, levonorgestrol, ethynodiol, levenorgestrel, norgestimate, gestanin, desogestrel, 3-keton-desogestrel, demegestone, promethoestrol, testosterone, spironolactone, and esters thereof, azole derivatives such as, e.g., imidazoles and mazoles and derivatives thereof, nitro compounds such as, e.g., amyl nitrates, nitroglycerine and isosorbide nitrates, amine compounds such as, e.g., pilocaine, oxyabutyninchloride, lidocaine, benzocaine, nicotine, chlorpheniramine, terfenadine, triprolidine, propanolol, metoprolol and salts thereof, oxicam derivatives such as, e.g., piroxicam, mucopolysaccharides such as, e.g., thiomucasee, opoid compounds such as, e.g., morphine and morphine-like drugs such as buprenorphine, oxymorphone, hydromorphone, levorphanol, hydrocodone, hydrocodone bitratrate, fentanyl and fentany derivatives and analogues, prostaglandins such as, e.g., a member of the PGA, PGB, PGE, or PGF series such as, e.g., misoprostol or enaprostil, a benzamide such as, e.g., metoclopramide, scopolamine, a peptide such as, e.g., growth hormone releasing factors, growth factors (epidermal growth factor (EGF), nerve growth factor (NGF), TGF, PDGF, insulin growth factor (IGF), fibroblast growth factor (aFGF, bFGF. etc.), and the like), somatostatin, calcitonin, insulin, vasopressin, interferons, IL-2, urokinase, serratiopeptidase, superoxide dismutase (SOD), tryrotropin releasing hormone (TRH), luteinizing hormone releasing hormone (LH-RH), corticotropin releasing hormone (CRF), growth hormone releasing hormone (GHRH), oxytocin, erythropoietin (EPO), colony stimulating factor (CSF), and the like, a xanthine such as, e.g., caffeine, theophylline, a catecholamine such as, e.g., ephedrine, salbutamol, terbutaline, a dihydropyridine such as, e.g., nifedipine, a thiazide such as, e.g., hydrochlorotiazide, flunarizine, a sydnonimine such as, e.g., molsidomine, a sulfated polysaccharide such as, e.g., heparin.

The active substances mentioned above are also listed for illustrative purposes; the invention is applicable to pharmaceutical formulations regardless of the active substance or substances incorporated therein.

The concentration of the active substance in the cores depends on the active substance in question, its potency, the severity of the disease to be prevented or treated, the age and condition of the patient. Methods applicable to selecting relevant concentrations of active substance in the cores are well known for a person skilled in the art and may be performed according to established guidelines for good clinical practice (GCP) or Investigational New Drug Exemption ("IND") regulations as described in e.g. Drug Applications, Nordic Guidelines, NLN Publication No. 12, Nordic Council on Medicines, Uppsala 1983 and Clinical Trials of Drugs, Nordic Guidelines, NLN Publication No. 11, Nordic Council on Medicines, Uppsala 1983. A person skilled in the art would by use of methods described in standard textbooks, guidelines and regulations as described above as well as common general knowledge within the field be able to select the exact dosage regimen to be implemented for any selected active substance and dosage form using merely routine experimentation procedures.

Coating

As it is apparent from the above, a particulate formulation according to the invention preferably comprises coated cores. The coating applied on the cores may in principle be any coating such as, e.g, a film coating, a sugar coating, a bioadhesive coating, or a so-called modified release coating. The coating provides e.g. the desired release profile of the active substance included in the cores or, alternatively, masks the taste of bad-tasting active substances, e.g. bitter tasting active substances such as, e.g., noscapine or theophylline. In some cases, the cores according to the invention may contain two or more layers of coating e.g. a first coating which governs the release rate of the active substance and a second layer which is bioadhesive. Other combinations of coatings than the one described above are of course also within the scope of the present invention.

As mentioned above, the coating may provide the cores with the desired properties with respect to release of the active substance, taste-masking, and/or bioadhesiveness. Thus, pharmaceutical formulations according to the present invention may be designed to release the active substance substantially immediately upon administration (the cores may be coated or uncoated) or at any suitable time or time period after administration. The latter type of formulations are generally known as modified release formulations.

In accordance with the United States Pharmacopoeia, the term "modified release dosage forms" includes two types of dosage form, namely "extended-release" dosage forms and "delayed-release" dosage form. An extended-release dosage form is defined as one that allows at least a twofold reduction in dosing frequency as compared to that drug presented as a conventional dosage form (i.e. as a solution or a prompt drug-releasing conventional solid dosage form). A delayed-release dosage form is defined as one that releases a drug (or drugs) at a time other than promptly after administration. Enteric coated formulations are delayed-release dosage forms.

In the present context, the term "modified release formulation" embraces the above-mentioned "extended-release" and "delayed-release" dosage forms and, accordingly, the following types of formulation are also included in the definition of the term "modified release formulation":

i) formulations which create a substantially constant concentration of the active substance within the body over an extended period of time, ii) formulations which after a predetermined lag time create a substantially constant concentration of the active substance within the body over an extended period of time, iii) formulations which sustain the action of the active substance (such as a drug substance) during a predetermined time period by maintaining a relatively constant, effective drug level in the body and at the same time minimizing the incidence of undesirable side effects associated with fluctuations in the plasma level of the active substance (sawtooth kinetic pattern), iv) formulations which attempt to localise drug action by, e.g., spatial placement of a modified release formulation adjacent to or in the diseases tissue or organ, v) formulations which attempt to target drug action by using carriers or chemical derivatives to deliver the active substance to a particular target cell type, and vi) formulations which are coated with an enteric coating ("gastro-resistant", "enterosoluble", "entero-coated", or simply "enteric" formulations).

Modified release formulations may also be denoted "extended release", "delayed release", "controlled release", "sustained release", "prolonged release", "programmed release", "time release", "rate-controlled", and/or "targeted release" formulations.

A suitable coating for a formulation according to the invention may, for example be:

a film coating, e.g. a coating based on one or more of the material selected from the following: hydroxypropylmethylcellulose, ethylcellulose, methylcellulose, hydroxyethylmethylcellulose, hydroxypropylcellulose, carboxymethylcellulose sodium, acrylate polymers (such as, e.g. Eudragit® E), polyethylene glycols and polyvinylpyrrolidone;

a sugar coating;

a bioadhesive coating, such as, e.g., a coating comprising a bioadhesive substance such as, e.g. a fatty acid ester such as, e.g., fatty acid esters wherein the fatty acid component of the fatty acid ester is a saturated or unsaturated fatty acid having a total number of carbon atoms of from $C_8$ to $C_{22}$; specific examples are glyceryl monooleate, glyceryl monolinoleate, glycerol monolinolenate, or mixtures thereof.

a modified release coating, such as, e.g., an enteric coating, e.g. a coating which is such that when the coated cores is swallowed by a human or an animal, it will be substantially unaffected by the chemical, enzymatic and other conditions prevailing within the stomach during passage through this part of the digestive system, but will substantially dissolve or otherwise disintegrate within the intestinal tract of the human or animal in question, thereby releasing the active substance within the intestines. An enteric coating may be based on one or more of the material selected from the following: methacrylic acid copolymers (e.g. Eudragit® L or S), cellulose acetate phthalate, ethylcellulose, hydroxypropylmethylcellulose acetate succinate, polyvinyl acetate phthalate, and shellac; or a modified release coating, e.g. a coating based on one or more materials selected from the following: shellac; waxes such as, e.g., beeswax, glycowax, castor wax, carnauba wax; hydrogenated oils such as, e.g., hydrogenated castor oil, hydrogenated coconut oil, hydrogenated rape seed oil, hydrogenated soyabean oil; fatty acid or fatty alcohol derivatives such as, e.g, stearyl alcohol, glyceryl monostearate, glyceryl distearate, glycerol palmitostearate; acrylic polymers such as, e.g., acrylic resins (Eudragit® RL and RS acrylic resins are copolymers of acrylic and methacrylic acid esters with a low content of quaternary ammonium groups) poly (methyl methacrylate), methacrylate hydrogels, ethylene glycol methacrylate; polylactide derivatives such as, e.g., dl-polylactic acid, polylactic-glycolic acid copolymer; cellulose derivatives, such as, e.g., ethylcellulose, cellulose acetate, cellulose propionate, cellulose butyrate, cellulose valerate, cellulose acetate propionate, cellulose acetate butyrate; vinyl polymers such as, e.g., polyvinyl acetate, polyvinyl formal, polyvinyl butyryl, vinyl chloride-vinyl acetate copolymer, ethylene-vinyl acetate copolymer, vinyl chloride-propylene-vinyl acetate copolymer, polyvinylpyrrolidone; glycols such as, e.g., 1,3-butylene glycol, polyethylene glycols; polyethylene; polyester; polybutadiene; and other high molecular synthetic polymers.

The coating material may be admixed with various excipients such as, e.g., plasticizers; anti-adhesives such as, e.g., colloidal silicium dioxide (fumed silica), talc, and magnesium stearate; colourants; and solvents in a manner known per se.

Examples of plasticizers for use in accordance with the invention include polyhydric alcohols such as, e.g., propylene glycol, glycerol, and polyethylene glycol; acetate esters such as, e.g., glyceryl triacetate (Triacetin), triethyl acetate, and acetyl triethyl acetate; phthalate esters such as, e.g., diethylphthalate; glycerides such as, e.g., acetylated monoglycerides; oils such as, e.g., castor oil, mineral oil, and fractionated coconot oil; and dibutyl sebacate.

The coating is applied on the cores from a solution and/or suspension in an organic solvent or in an aqueous medium. Employment of an aqueous medium is preferred due to safety, economy and environment. Examples of suitable organic solvents for use in coating the cores according to the invention are alcohols such as, e.g., methanol, ethanol, isopropanol, and propanol; ketones such as, e.g. acetone, and toluene; esters such as, e.g., ethyl acetate, and ethyl lactate; chlorinated hydrocarbons such as, e.g. methylene chloride, and 1:1:1 trichloroethane.

The application of the coating may be performed in a fluidized bed but any suitable coating apparatus may be applied such as those well known by a person skilled in the art (e.g. pan coating, spray-drying, electrostatic coating etc.). When the cores are coated in a fluidized bed apparatus it has proved advantageous to apply the coating composition from a nozzle positioned in the bottom of the fluid bed apparatus, i.e. having the flow of the liquid (the coating composition) and the fluidizing air in a mixed flow except when the coating is performed with a fat or a wax. By using a mixed flow it has shown possible to coat relatively small particles without agglomeration.

The amount of coating applied on the cores depends inter alia on the size of the cores, the type of coating employed, the type of the active substance employed, and the desired release pattern.

The friability of the coated cores (weight loss in % w/w, determined as described herein) is at the most about 20% w/w. Preferably, the friability is at the most about 10% w/w such as, e.g., at the most about 8% w/w, 7% w/w, 6% w/w, 5% w/w or even as low as at the most about 1–2% w/w.

In some cases, the inventors have found that the uncoated cores in themselves are suitable for use in pharmaceutical formulations. This is especially the case when the formulation is presented in the form of formulations which are adapted to administration via the oral, buccal, mucosal, nasal, rectal, vaginal, or topical route or to administration to wounds, in particular when the formulation is adapted for nasal administration. Accordingly, the present invention also relates to a pharmaceutical multiple unit particulate formulation comprising individual units in the form of cores, each core comprising i) a pharmaceutically acceptable inert carrier which is present in the core in a first concentration of at least about 20% w/w calculated on the total weight of the core, and which is selected from the group consisting of calcium carbonate, calcium silicate, calcium magnesium silicate, calcium phosphate, kaolin, sodium hydrogen carbonate, sodium sulfate, barium carbonate, barium sulfate, magnesium sulfate, magnesium carbonate, and activated carbon, and ii) an active substance, the pharmaceutically acceptable inert carrier being such a material which—when formulated into uncoated cores containing the pharmaceutically acceptable inert carrier optionally in combination with a binder and with a second concentration of the inert carrier of at least 80% w/w calculated on the total weight of the uncoated core—has a friability (weight loss in % w/w) of at the most about 20%, when tested as described herein, and the cores have a flow angle—when tested according to method A described herein using a diameter of the disc outlet of 9 mm—of at the most 30°.

The above-mentioned uncoated cores according to the invention have a remarkable flowability in themselves i.e. without any coating. Thus, the uncoated cores have a flow angle—when tested according to method A described in the experimental section herein—of at the most about 30° such as at the most about 25°, about 20°, about 15°, about 10°, or about 80° (The same considerations apply for the coated cores according to the invention). The excellent flowability makes them especially suitable for use in those cases where a coating may delay the effect of the active substance. Accordingly, the uncoated cores are especially suitable for use in formulations according to the invention when a prompt response of the active substance is required such as, e.g., in the case of nasal or buccal administration.

Pharmaceutically Acceptable Excipients—Dosage Forms

The active substance comprised in the cores may either be present in admixture with the pharmaceutically acceptable inert carrier, or it may be applied on inert cores comprising the pharmaceutically acceptable inert carrier, optionally in admixture with one or more pharmaceutically acceptable excipients (see below). In the latter case, the active substance may be applied by means of methods well known by a person skilled in the art such as, e.g., a fluidized bed method. In the thus prepared cores, the active substance is present in a layer on the outer surface of the uncoated or coated cores.

Apart from the active substance and the pharmaceutically acceptable inert carrier, the pharmaceutical formulations according to the invention may comprise pharmaceutically or cosmetically acceptable excipients. The pharmaceutically acceptable excipient for use in a particulate formulation according to the invention is generally selected from the group consisting of fillers, binders, disintegrants, glidants, and lubricants; in the following is given a more detailed list of suitable pharmaceutically acceptable excipients for use in formulations according to the invention.

A pharmaceutical formulations according to the invention may be adapted to administration via the oral, buccal, mucosal, nasal, rectal, vaginal, or topical route or to wounds.

In other aspects, the present invention relates to solid dosage forms or liquid compositions comprising a pharmaceutical particulate formulation according to the invention. Such dosage forms or other suitable compositions (e.g. tablets, capsules, mixtures, sprays etc.) according to the invention may be formulated according to conventional pharmaceutical practice, see, e.g., "Remington's Pharmaceutical Sciences" and "Encyclopedia of Pharmaceutical Technology", edited by Swarbrick, J. & J. C. Boylan, Marcel Dekker, Inc., New York, 1988.

In the following is given a review on relevant pharmaceutical compositions according to the invention. The review is based on the particular administration route. However, it is appreciated that in those cases where a pharmaceutically acceptable excipient may be employed in different dosage forms or compositions, the application of a particular pharmaceutically acceptable excipient is not limited to a particular dosage form of a particular function of the excipient.

The choice of pharmaceutically acceptable excipient(s) in a formulation according to the invention and the optimum concentration thereof cannot generally be predicted and must be determined on the basis of an experimental evaluation of the final formulation.

Formulations for oral use

Formulations according to the invention are very suitable for oral administration either in the form of a particulate formulation or in the form of a solid, semi-solid or liquid dosage form.

Firstly, the individual units (the cores) are contemplated to have a particle size which enable the particles to pass the gastro-intestinal tract independently of the amount of e.g. food in the stomach and its influence on the gastric transit time. This property makes it possible to achieve an effect of the active substance within a predetermined time period and at a time at which a patient normally is unable to take any medication (e.g. during sleep).

Secondly, a formulation according to the invention contains cores of such a small particle size that it is possible to present the formulation in a unit dosage form which easily may be divided into two or more dosages without any destruction of the properties of the formulation (e.g. the release characteristics).

Thirdly, a formulation according to the invention may be presented in a liquid form comprising the individual cores dispersed in a liquid medium. Such a formulation may be a modified-release formulation due to the particular coating of the individual cores and an advantageous and economic alternative to the modified-release liquids presently on the marked. Furthermore, a liquid formulation according to the invention is easy to prepare. A liquid formulation according to the invention is also convenient for administration to children and elder subjects. In fact, oral administration of a liquid formulation to pediatric and/or geriatric patients is often the only possibility because such patients often have difficulties in swallowing a tablet or a capsule.

A modified release liquid formulation as referred to above may, e.g., comprise a pharmaceutical multiple unit particulate formulation according to the invention, e.g. in the form of inert cores covered firstly by a layer comprising an active substance and secondly by a modified release layer such as an enteric coating. Subsequently such a formulation may be admixed with pharmaceutically acceptable excipients such as, e.g., flavouring agents, thickening agents, preservatives, colouring agents, pH-adjusting agents etc. and then be subjected to a granulation process in order to obtain granules which easily can be presented dispersed in a suitable liquid as a relatively stable composition. The above-mentioned example of a modified release liquid is not construed to limit the invention in any way; another alternative is, e.g., to employ cores which in themselves comprise the active substance and upon which a modified release layer is applied.

Moreover, it is possible to provide a formulation according to the invention with a bioadhesive coating whereby a drug delivery system is obtained which is contemplated to release the active substance during a 24-hour period. Such a formulation is a so-called "once-daily" formulation, i.e. a formulation which should be administered only once a day. The advantage of a "once-daily" formulation is that patient compliance will be improved compared to a formulation which must be administered two or more times daily.

Formulations for oral use include solid dosage forms such as, e.g., powders, granules, sachets, tablets, capsules, effervescent tablets, chewable tablets, lozenges, immediate release tablets, and modified release tablets as well as fluid or liquid formulations such as, e.g. powders, dispersible powders, or granules suitable for preparation of an aqueous suspension by addition of an aqueous medium, emulsions, dispersions, and mixtures.

Solid dosage forms for oral use

The formulation contain the active substance and the inert carrier optionally in admixture with one or more pharmaceutically acceptable excipient. These excipients may be, for example, inert diluents or fillers, such as sucrose, sorbitol, sugar, mannitol, microcrystalline cellulose, starches including potato starch, calcium carbonate, sodium chloride, lactose, calcium phosphate, calcium sulfate, or sodium phosphate;

granulating and disintegrating agents, for example, cellulose derivatives including microcrystalline cellulose, starches including potato starch, croscarmellose sodium, alginates, or alginic acid;

binding agents, for example, sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone such as, e.g, PVP K12, PVP K15, PVP K17, PVP K25, PVP K30, PVP K60, PVP K90, or PVP K120, or combinations thereof, polyvinylacetate, or polyethylene glycol; and lubricating agents including glidants and antiadhesives, for example, magnesium stearate, zinc stearate, stearic acid, silicas, hydrogenated vegetable oils, or talc.

Other pharmaceutically acceptable excipients can be colorants, flavouring agents, plasticizers, humectants, buffering agents etc.

In those cases where the pharmaceutical formulation is in the form of a solid dosage form in unit dosage form (e.g. a tablet or a capsule), the unit dosage form may be provided with a coating like one or more of the coatings mentioned below.

The coating may be applied on the unit dosage form in a similar manner as that described in "Aqueous film coating" by James A. Seitz in "Encyclopedia of Pharmaceutical Technology", Vol 1, pp. 337–349 edited by Swarbrick, J. & J. C. Boylan, Marcel Dekker, Inc., New York, 1988.

Fluid/liquid compositions for oral use

Formulation as a suspension, an emulsion or a dispersion provides the active substance in admixture with a dispersing or wetting agent, suspending agent, and/or one or more preservatives. Such formulations may also be suitable for use in of an active substance to e.g. a mucosa such as the gastrointestinal, buccal, nasal, rectal, or vaginal mucosa, or for administration to intact or damaged skin, or wounds.

Suitable dispersing or wetting agents are, for example, naturally occurring phosphatides, e.g., lecithin, or soybean lecithin; condensation products of ethylene oxide with e.g. a fatty acid, a long chain aliphatic alcohol, or a partial ester derived from fatty acids and a hexitol or a hexitol anhydride, for example polyoxyethylene stearate, polyoxyethylene sorbitol monooleate, polyoxyethylene sorbitan monooleate etc.

Suitable suspending agents are, e.g., naturally occurring gums such as, e.g., gum acacia, xanthan gum, or gum tragacanth; celluloses such as, e.g., sodium carboxymethylcellulose, microcrystalline cellulose (e.g. Avicel® RC 591, methylcellulose; alginates such as, e.g., sodium alginate, etc.

Suitable examples of preservatives for use in formulations according to the invention are parabens, such as methyl or propyl p-hydroxybenzoate, and benzalkonium chloride.

Rectal and/or vaginal formulations

For application to the rectal or vaginal mucosa suitable formulations for use according to the invention include suppositories (emulsion or suspension type), enemas, and rectal gelatin capsules (solutions or suspensions). Appropriate pharmaceutically acceptable suppository bases include cocoa butter, esterified fatty acids, glycerinated gelatin, and various water-soluble or dispersible bases like polyethylene glycols and polyoxyethylene sorbitan fatty acid esters. Various additives like, e.g., enhancers or surfactants may be incorporated.

Nasal formulations

For application to the nasal mucosa, nasal sprays and aerosols for inhalation are suitable compositions for use according to the invention. In a typically nasal formulation, the active substance is present in the form of a particulate formulation optionally dispersed in a suitable vehicle. The pharmaceutically acceptable vehicles and excipients and optionally other pharmaceutically acceptable materials present in the composition such as diluents, enhancers, flavouring agents, preservatives etc. are all selected in accordance with conventional pharmaceutical practice in a manner understood by the persons skilled in the art of formulating pharmaceuticals.

Nasal administration may be employed in those cases where an immediate effect is desired. Furthermore, after administration of a nasal formulation according to the invention, the active substance may be adsorped on the nasal mucosa. The adsorption to the mucosa is believed to lead to a less irri-tative effect than when e.g. a liquid vehicle e.g. containing a penetration enhancer or promoter is employed.

Topical formulations

For application to the skin, the formulations according to the invention may contain conventionally non-toxic pharmaceutically acceptable carriers and excipients including microspheres and liposomes. The formulations include creams, ointments, lotions, liniments, gels, hydrogels, solutions, suspensions, sticks, sprays, pastes, plasters, and other kind of transdermal drug delivery systems. The pharmaceutically acceptable excipients may include emulsifying agents, antioxidants, buffering agents, preservatives, humectants, penetration enhancers, chelating agents, gel-forming agents, ointment bases, perfumes, and skin protective agents.

Examples of emulsifying agents are naturally occurring gums, e.g. gum acacia or gum tragacanth, naturally occurring phosphatides, e.g. soybean lecithin, and sorbitan monooleate derivatives.

Examples of antioxidants are butylated hydroxy anisole (BHA), ascorbic acid and derivatives thereof, tocopherol and derivatives thereof, butylated hydroxy anisole, and cysteine.

Examples of preservatives are parabens, such as methyl or propyl p-hydroxybenzoate, and benzalkonium chloride.

Examples of humectants are glycerin, propylene glycol, sorbitol, and urea.

Examples of penetration enhancers are propylene glycol, DMSO, triethanolamine, N,N-dimethylacetamide, N,N-dimethylformamide, 2-pyrrolidone and derivatives thereof, tetrahydrofurfuryl alcohol, and Azone®.

Examples of chelating agents are sodium EDTA, citric acid, and phosphoric acid.

Examples of other excipients are edible oils like almond oil, castor oil, cacao butter, coconut oil, corn oil, cottonseed oil, linseed oil, olive oil, palm oil, peanut oil, poppyseed oil, rapeseed oil, sesame oil, soybean oil, sunflower oil, and teaseed oil; and of polymers such as carmelose, sodium carmelose, hydroxypropylmethylcellulose, hydroxyethylcellylose, hydroxypropylcellulose, chitosane, pectin, xanthan gum, carragenan, locust bean gum, acacia gum, gelatin, and alginates.

Examples of ointment bases are beeswax, paraffin, cetyl palmitate, vegetable oils, sorbitan esters of fatty acids (Span), polyethylene glycols, and condensation products between sorbitan esters of fatty acids and ethylene oxide, e.g. polyoxyethylene sorbitan monooleate (Tween).

The formulations mentioned above for topical administration may also be applied to wounds or they may be suitable for direct application or for introduction into relevant orifice(s) of the body, e.g. the rectal, urethral, vaginal or oral orifices. The formulation may simply be applied directly on the part to be treated such as, e.g., the mucosa.
Preparation of a Formulation According to the Invention The invention also relates to a process for the preparation of a pharmaceutical multiple unit particulate formulation according to the invention, the process comprising the steps of i) preparing a liquid medium optionally comprising one or more pharmaceutically acceptable excipients, ii) adding to the resulting liquid medium the pharmaceutically inert carrier and the active substance to obtain a feed, iii) optionally adding further pharmaceutically acceptable excipients, iv) mixing the feed obtained from step ii) or iii), v) drying the resulting feed from step iv) to obtain cores, and vi) coating the cores obtained from step v).

In a preferred embodiment, the the drying step v) is performed by means of spray-drying.

A formulation according to the invention may also comprise inert cores onto which the active substance is applied. Such a formulation may be prepared by means of a process comprising the steps of i) preparing a liquid medium optionally comprising one or more pharmaceutically acceptable excipients, ii) adding to the resulting liquid medium the pharmaceutically inert carrier to obtain a feed, iii) optionally adding further pharmaceutically acceptable excipients, iv) mixing the feed obtained from step ii) or iii), v) drying the resulting feed from step iv) to obtain cores, vi) applying on the cores the active substance, and vii) coating the cores obtained from step vi).

In a preferred embodiment, the drying step v) and/or the step vi) of the process according to the invention are performed by means of spray-drying.

As will be understood, details and particulars concerning the formulation aspect, the uncoated core aspect, and the process aspects of the invention will be the same as or analogous to the details and particulars concerning the aspects discussed above, and this means that wherever appropriate, the statements above concerning the pharmaceutical multiple unit particulate formulations, their preparation, improved properties and uses apply mutatis mutandis to the other aspects of the invention.

MATERIALS

Materials employed in the Examples below are given in the following. If possible, the grade employed of a material stated in the list below was of pharmacopoeia grade. In those cases where reference is given to an official pharmacopoeia, the reference is to the current edition of the stated pharmacopoeia.

The following abbreviations are used:

| Ph. Eur.: | European Pharmacopoeia |
|---|---|
| USP: | United States Pharmacopoeia |

Inert Carrier Material

Calcium carbonate was Faxe Kalk Microstevns (0–20 μm) supplied by Faxe Kalk, Denmark or a pharmacopoeial grade (Ph. Eur.) obtained from Nomeco, Denmark Calcium sulfate was calcii sulfas, Ph. Eur. from Nomeco, Denmark Magnesium oxide was magnesii oxidum, Ph. Eur. from Nomeco, Denmark Active Substance Theophylline was of pharmacopoeia grade and supplied by Nomeco, Denmark Binders Polyvinylpyrrolidon was PVP 29-32, such as PVP K30, supplied by Nomeco, Denmark PVA (polyvinylacetate) was Mowiol® from Hoechst, United Kingdom Sodium carboxymethylcellulose from P. Brøste A/S, Denmark Diluents/Disintegrants Avicel pH 101 (Microcrystalline cellulose) from Aktiebolaget Montoil, Sweden Lubricants/Glidants Magnesium stearate from Aktiebolaget Montoil, Sweden Polyethylene glycol, PEG 6000 from Nordisk Droge Handel A/S, Denmark Microtalcum from Bønnelycke, Denmark or from Merck, Darmstadt, Germany Other Types of Excipients (e.g. sweeteners, gas forming agents, etc.)

Sorbitol from Cerestar Scandinavia, Denmark

Citric acid (serving as an acid source for effervescent reaction) from Nordisk Droge Handel A/S, Denmark Sodium hydrogen carbonate (serving as a carbon dioxide source for effervescent reaction) from Nordisk Droge Handel A/S, Denmark Instant sugar from Sukkerfabrikkerne, Denmark Viscosity-Increasing Agents Avicel® RC 591, microcrystalline cellulose from Aktiebolaget Montoil, Sweden Xanthan gum from Kelco International Ltd., Girvan KA 93N, Ayrshire, Scotland Anti-Foaming Agent Silicon oil from Wacker-chemie Danmark A/S, Denmark Antifoam M 10 from Kemoplast ApS, Denmark Coating Materials Surelease® from dolorcon Ltd, United Kingdom; Surelease® is an aqueous polymeric dispersion having the following composition:

| Polymer: | ethylcellulose |
|---|---|
| Plasticizer: | DBS (dibutylsebacetate) |
| Stabilizer: | oleic acid |
| Anti-adherent: | fumed silica |
| Aqueous base: | ammonium hydroxide solution |
| Total solid content: | 25% w/w |

Ethylcellulose 20 cps from Chr. Krogh A/S, Denmark

Glyceryl monooleate (monoolein, GMO), manufactured by Grindsted Products A/S, Denmark; the product used has a total content of fatty acid monoesters of at least about 96%. The product employed in the examples described herein had the following composition of fatty acid monoesters:

| Glyceryl monooleate | about 82% w/w |
|---|---|
| Glyceryl monolinoleate | about 8% w/w |
| Glyceryl monopalmitate | about 4% w/w |
| Glyceryl monostearate | about 4% w/w |

Eudragit® RS 30D as a 30% w/w dispersion in water was obtained from Rohm Pharma GmbH, Weiterstadt, Germany Plasticizers Dibutylsebacate from Sigma, U.S.A.

Triethyl citrate, Eudraflex® from Röhm Pharma GmbH, Weiterstadt, Germany

Solvent/Carrier

Water was employed in the form of distilled or otherwise purified water

APPARATUS AND METEODS

Spray Drying Equipment

A NIRO P-6.3N spray drying equipment was employed. The spray drier had a diameter of 2.0 m, a cylindrical height of 2.0 m and a 60° cone. In Example 1B, a APV Anhydro type 3K61 conical spray equipment was employed. In both apparatuses, a mono-pump for the pressure nozzle atomizer was placed at the bottom of the chamber with the spray pointing upwards.

Coating Equipment

A fluidized bed GPCG I/6' Wurster supplied by Glatt GmbH, Germany was employed.

Compression of Tablets

A DIAF TM 20 (Denmark) tabletting machine was employed

Particle Size Measurement

A Malvern System 2600 apparatus from England was employed measuring the mean particle size as well as the particle size distribution.

Apparent Volume—Bulk Density

The bulk density was measured by use of an apparatus according to Ph. Eur. V.5.5.4.1 obtained from J. Engelsmann AG, Apparatgebau, Ludvigshafen a. Rh., Germany. The apparatus contains a settling apparatus capable of producing in 1 min 250±15 taps from a height of 3±0.2 mm and a 250 ml graduated cylinder (2 ml intervals).

The bulk density is determined by introducing without compacting 100.0 g of the sample to be tested into the dry cylinder and proceeding as described in Ph. Eur.

The results obtained are expressed as apparent densities:

i) apparent density before settling or density of bulk product (also denoted poured density), and ii) apparent density after settling or density of settled product (also denoted tapped density).

True density

The true density was measured by use of a Micromeritics Accupyc 1350 apparatus employing helium as inert gas. The true density expresses the ratio between the mass of the solid particles and the actual volume thereof.

Residual Water

The content of residual water was either determined using a Karl Fischer titration method or by employing the following method determining the loss of drying.

Loss of Drying

The loss of drying was determined using a Mettler balance equipped with a heating unit. The loss of drying was determined after 10 minutes at a temperature of about 105° C. The weight of the sample (after drying to constant weight) at the start was defined as 100% and the weight of the sample after 10 minutes at about 105° C. and equilibration to room temperature was, e.g., X% then the weight loss and, accordingly, the loss of drying was (100-X)%.

Particle Form

The form of the particles was observed by microscopy. The visual inspection was furthermore employed for evaluation of the appearance of the surface of the particles and of any agglomeration of the particles. The visual inspection may also be employed to observe a balloon effect, i.e. whether the cores contain air-filled hollow spaces.

Flowability

A. Test using an Erweka type apparatus measuring the flow time and the flow angle The flowability of a particulate formulation was assessed by using an Erweka type GWF apparatus in accordance with the in instructions given from the manufacturer. A sample size weighing 30 g is employed and the diameter of the outlet of the disc used has a diameter of 9.0 mm. In some experiments, the flowability was also studied using disc having an outlet diameter of 6 and/or 12 mm, respectively.

The flowability is determined as the flow time, i.e. the time it takes for the sample to pass the apparatus, as well as the flow angle $\alpha$ which is calculated from the following equation:

$$\text{Tan } \alpha = (\text{flow time in sec})/\text{amount of sample in gram}$$

A small flow angle $\alpha$ indicates a good flowing powder (the smaller the flow angle is, the better is the flowability of the powder tested).

B. Test using an open cylindrical tube and determining the angle of repose

The flowability of a particulate formulation was assessed by using an open cylindrical tube having a diameter of about 3 cm and a height of about 3.5 cm. A sample of the formulation under testing was filled into the tube and placed on a smooth level surface. After filling, the tube is removed, and the angle of repose α is determined as the angle between the level surface and the powder pile (for further details see Lieberman, H. D., L. Lachman & J. B. Schwartz (Eds.): Pharmaceutical Dosage Forms: Tablets, Volume 2, Dekker, New York, pages 35 and 38). The method employed gives the static angle of repose, because the powder container is removed and the powder does not, or is not flowing before measurement.

The angle of repose α is also denoted the angle of slip and is a relative measure of the friction between the particles as well as a measure of the cohesiveness of the particles.

In general, a cohesive powder has an angle of repose of at least 40°, whereas a non-cohesive powder, i.e. a freely flowing powder has an angle of repose of at the most about 30°.

Crushing Strength

The crushing strength of tablets prepared was determined using an Erweka type apparatus TBH 28 from Erweka Apparatgebau GmbH, Heusenstamm, Germany. The crushing strength is given in kp as a mean of 10 tablets tested.

Friability Test

Friability test using an Erweka apparatus

The test method described in the following is a modified method of the test described by Stainmesse et al. in Conference Papers, Volume 2A, Apr. 13, 1994, pages 378–395 at the 13th Pharmaceutical Technology Conference, Strasbourg, France:

The cores are dedusted on a 90 μm sieve using an air jet sieve (Alpine Air Jet Sieves® 200 Laboratory Type from Alpine AG, Augsburg, Germany). To each of three 60 ml flasks (external diameter: 3.8 cm, height: 9.1 cm) are transferred 15.0 g of the thus dedusted cores and 5 g glass beads are introduced into each flask (the glass beads have a diameter of about 2 mm). The three flasks are placed on an Erweka friability apparatus by placing them in the smallest wheel (19 cm in diameter, see FIG. 1). The test is started and after 5 minutes at 20 rotations per minute, the cores from each flask are dedusted as before and weighed. The test is repeated but now with a test time period of 35 minutes in order to investigate whether the weight loss is dependant on the testing time. The loss of weight is calculated as a percentage of the initial weight.

With respect to inert cores for use according to the invention, i.e. cores based on the inert carrier material without any active substance, the friability (weight loss in % w/w) should be at the most about 20%, preferably at the most about 15%, such as, e.g. at the most about 14% or about 13%. With respect to a particulate formulation according to the invention, the friability for the cores comprised therein is at the most about 20%, preferably at the most about 15%, such as, e.g. at the most about 14% or 13%.

Dissolution Test

A Sotax USP apparatus was employed. The dissolution test was performed in accordance with USP, method 2 (paddle-method) and 50 rpm using a phosphate buffer solution, pH 7.5 (USP) as dissolution medium and a temperature of 37° C. In some cases the dissolution medium was 0.1 N hydrochloric acid during the first 2 hours of testing; then the medium was adjusted to pH 6.8 by addition of $Na_3PO_4$.

900 ml of dissolution medium were placed into each of the 6 vessels of the Sotax apparatus employed. The temperature was controlled thermostatically at 37° C.±0.5° C. In those cases where the sample under testing was a tablet, one tablet was placed into each vessel and the test was started. In those cases where the sample under testing was a sample of a particulate formulation according to the invention, an accurately weighted amount corresponding to one dose of the active substance was placed in each vessel and the test was started. At appropriate intervals a 10 ml sample was removed from each vessel for individual measurement (and replaced with another 10 ml of dissolution medium). The samples were filtered and cooled to room temperature and analyzed. In those cases where the active substance employed in the formulation under testing was theophylline, the analysis was performed by means of UV spectrometry at a wavelength setting of about 272 nm.

Viscosity Determination

The dynamic viscosity of a sample is determined using a Rotovisco CV 100, HAAKE (Germany) equipped with a RV 100 "printer", HAAKE (Germany). The measurements are performed at 25° C.±0.2° C. at a shear rate ramp of 0–300 $sec^{-1}$ using a ZA30 cup and cylinder. The mixture is presheared before measuring by turning the sample 3 times prior to the measurement. A flow curve is obtained and the results is read on the down curve. Tixotropi is identified by the presence of hysteresis on the flow curve.

Test System for Bioadhesion by Means of Rabbit Jejunm Membranes

The test system for bioadhesion described in the following is a modified system of a method described by Ranga Rao & Buri (Int. J. Pharm. 1989, 52, 265–270).

Male albino rabbits (3–4 kg, New Zealand white rabbit SSC: CPH) was fasted for 20 hours before they were killed by means of a pentobarbital sodium injection. The intestines of the rabbits were dissected and placed in an isotonic 0.9% sodium chloride solution at room temperature (about 18° C.). Within 30 minutes the jejunums were gently rinsed with the saline until the intestines were clear. The jejunums were cut into pieces of about 8–9 cm in length and frozen (-20° C.) immediately. The jejunums were stored up to 3 months before use. Before testing, the segment of jejunum was gently thawed out.

The segment of the jejunum was cut longitudinally. It was placed on a stainless steel support (a tube of 2 cm in diameter and cut longitudinally at its centre) with the mucosa layer upside, spread and held in position on the support by the adhesive effect of the jejunum itself. The support with the jejunum was placed at an angle of -7° in a cynlindrical cell thermostated at 37° C. The relative humidity was kept at about 100%. The jejunum was then flushed with a medium of 0.02 M isotonic phosphate buffer solution (pH 6.5, 37° C.) for 2 minutes at a flow rate of 5 ml/min, using a peristaltic pump. An accurately weighed amount of the sample to be tested for bioadhesive properties was placed evenly on the mucosa of the jejunum (about 0.8×6 cm) (before applying the sample, the area onto which the sample should be applied was marked with indian ink). Optionally, 1 ml of the buffer solution was carefully dropped evenly on the sample applied. Immediately after, the segments were left for 10 minutes in the cell allowing the sample to interact with the glycoproteins of the jejunum and to prevent drying of the mucus. After 10 minutes, the segments were flushed evenly with the isotonic 0.02 M phosphate buffer solution (pH 6.5, 37° C.) for 30 minutes at a flow rate of 5 ml/min. The tip of the tube carrying the buffer solution was placed 3–4 mm above the jejunum to ensure an even liquid flow over the mucosa. The washings were collected into a beaker. The amount of bioadhesive component remaining on the jejunum was calculated either by measuring the amount of sample in the beaker or by measuring the amount of sample remaining in the jejunum by means of a suitable analysis method, e.g. by HPLC.

The formulation tested is considered to be bioadhesive if the residual amount (of glyceryl monooleate) is at least about 40% w/w such as at least about 45% w/w, about 50% w/w, 55% w/w, or 60% w/w.

EXAMPLES

The invention is further illustrated by the following working examples. The examples are not intented to limit the invention.

Example 1A

Preparation of Inert Calcium Carbonate Cores for Use According to the Invention

A suspension was prepared from the following ingredients:

TABLE 1

| Ingredients | kg | % w/w in suspension | % w/w dry matter |
|---|---|---|---|
| Calcium carbonate | 20 | 35.1 | 96 |
| PVP (Povidon, Mecol) | 0.8 | 1.5 | 4 |
| Distilled water | 32.7 | 65.4 | |

The values given in the last column of Table 1 given above state the % w/w dry matter in the suspension.

PVP (polyvinylpyrrolidone) (0.8 kg) which in this case functions as a binder is dissolved in warm water (8 kg) at a temperature of about 50° C. so that the PVP concentration corresponds to 10% w/w. The remaining amount of water (i.e. 24.7 kg) is then added under stirring. 20 kg of calcium carbonate is then added to the mixture under stirring and the resulting mixture containing a suspension of calcium carbonate in water is immediately before use sieved through a 177 μm sieve. The resulting suspension, i.e. the feed, is manually stirred at regular intervals to ensure a homogeneous feed.

The homogen feed is sprayed into the above-mentioned NIRO P-6.3N spray drying equipment using a pressure nozzle atomizer positioned at the bottom of the chamber and with the spray pointing upwards in order to obtain as small particles as possible. The following process parameters are employed:

| Inlet temperature: | 330° C. |
|---|---|
| Outlet temperature: | 127° C. |
| Fluidising air velocity: | 650 kg/hour |

The resulting calcium carbonate cores are spherical pellets having a mean particle size of 122 μm, i.e. 50% w/w of the pellets have a size which is larger than 122 μm and 50% w/w of the particle have a size which is 122 μm or below. The particle size was measured by means of the Malvern System 2600 apparatus and the following results were obtained:

i) about 10% w/w of the particles have a size of less than 15 μm, ii) about 50% w/w of the particles have a size of less than 122 μm, and iii) about 90% w/w of the particles have a size of less than 167 μm.

The apparent densities of the calcium carbonate pellets were determined; the poured density was 0.71 g/ml (determined as $m/V_0$, cf. Ph. Eur.) and the tapped density was 0.84 g/ml ($m/V_{250}$, cf. Ph. Eur., i.e. measured after compaction 250 times).

The friability was determined as described herein and found to be 6.0% w/w and 6.4% w/w after a testing time of 5 minutes and 35 minutes, respectively.

The flowability was also determined using method A as described herein and the flow time was found to be 2.92 sec and the flow angle 5.270°. Using method B as described herein, an angle of repose of 21° was found.

The loss of drying was determined to be 2.2% w/w. In this connection it can be mentioned that it is generally observed that particles having a relatively high loss of drying are susceptible to instability and/or have a tendency to agglomerate and, furthermore, that particles having no loss of drying have a tendency of being too brittle. However, in the present case, the inventors have found that it is possible to coat pellets prepared according to the invention even when the particles have a very small, if any, content of water.

Example 1B

Preparation of Inert Calcium Carbonate Cores for Use According to the Invention

A suspension was prepared as described in the above Example 1A. The homogen feed is sprayed into a APV Anhydro type 3K61 conical spray equipment using a pressure nozzle atomizer positioned at the bottom of the chamber and with the spray pointing upwards in order to obtain the largest particles. The following process parameters are employed:

| Inlet air temperature: | 350.0° C. |
|---|---|
| Outlet air temperature: | 125.0° C. |

The resulting calcium carbonate cores are spherical pellets having a tapped density (bulk density) of 0.89 g/ml measured after compaction 250 times. The flowability expressed as the flow time and the flow angle, respectively, was 2.42 sec and 4.30°, respectively (method A described herein was employed). An angle of repose of 22° was found using method B described herein. The friability was determined to be 12.2% after a testing time of 5 minutes and 11.1% after a testing time of 35 minutes. The loss of drying was determined to be 0.43% w/w.

Example 1C

Preparation of Inert Cores

Inert cores were prepared as described in the above Example 1B employing the process parameters given in Table I below:

TABLE I

| Batch | Substance | % w/w dry matter | % w/w in suspension | Air temperature Inlet | Air temperature Outlet | Nozzle pressure (Bar) |
|---|---|---|---|---|---|---|
| BFE 1 | $CaCO_3$, FAXE | 4 | 37 | 355 | 120 | 27 |
| BFE 2 | $CaCO_3$, FAXE | 4 | 37 | 355 | 105 | 40 |
| BFE 4 | $CaCO_3$, NOMECO | 4 | 29,3 | 355 | 120 | 15–29 |
| BFE 5 | $CaCO_3$, NOMECO | 4 | 29,3 | 340 | 190 | 10–15 |
| BFE 7 | $CaCO_3$, FAXE | 6 | 48,6 | 350 | 104 | 40 |
| BFE 8 | $CaCO_3$, FAXE | 8 | 48,1 | 350 | 104 | 40 |
| BFE 9 | $CaCO_3$, FAXE | 4 | 59 | 370 | 103 | 40 |
| BFE 10 | $CaSO_4$ | 4 | 49,8 | 350 | 104 | 40 |
| BFE 12 | $CaCO_3$, FAXE | 6 | 48,6 | 340 | 104 | 40 |
| BFE 13 | $CaCO_3$, NOMECO | 6 | 31,2 | 400 | 175 | 38 |
| BFE 14 | $CaCO_3$, NOMECO | 8 | 30,3 | 400 | 175 | 38 |
| BFE 15 | MgO | 4 | 20 | 320 | 120 | 40 |

The properties of the inert cores are given in Table II below. The flow angle was determined using method A described herein, but employing discs having an outlet diameter of 6.0, 9.0, and 12.0 mm, respectively.

TABLE II

| Batch | Residual water | Median | Particle size | Flow angle° x |
|---|---|---|---|---|
| BFE 1 | 0,71% | 95 µm | approx. 50% between 90–180 | 14,4/4,6/0,56 |
| BFE 2 | 3,68% | 128 µm | approx. 55% | 26,9/8,2/0,48 |
| BFE 4 | 18,7% | 18 µm | approx. 25% | —/21,4/1,7 |
| BFE 5 | 16,0% | 15 µm | approx. 25% | 50,8/16,3/1,4 |
| BFE 7 | 0,76% | 104 µm | approx. 80% | 13,8/4,27/0,5 |
| BFE 8 | 0,60% | 100 µm | approx. 73% | 16,2/5,6/0,55 |
| BFE 9 | 1,37% | 132 µm | approx. 62% | 13,5/5,2/0,5 |
| BFE 10 | 5,62% | 81 µm | approx. 72% | 15,3/5,9/1,3 |
| BFE 12 | 1,04% | 110 µm | approx. 60% | 13,2/4,2/0,5 |
| BFE 13 | 0,51% | * | approx. 75% | 42,4/18,2/2,5 |
| BFE 14 | 0,64% | * | approx. 79% | 39,1/15,3/2,2 |
| BFE 15 | 0,30%+ | * | approx. 60% | 20,2/8,5/1,8 |

°values for 5 min and 35 min
x (diameter 6, 9, 12 mm) mean of three measurings in degrees
+measured as loss of drying
*not determined due to solvate formation The inert cores were also inspected visually by microscopy and the following results were found:

| | |
|---|---|
| BFE 1: | Microscopy: Spherical pellets with some variation with respect to size |
| BFE 2: | Appears as a moist powder with some agglomeration |
| BFE 4: | Microscopy: Pellets of different sizes |
| BFE 5: | Like BFE 4 |
| BFE 7: | Spherical pellets |
| BFE 8: | Spherical pellets with a tendency of agglomeration |
| BFE 9: | Spherical pellets but varying in size compared with batch BFE 7 |
| BFE 10: | Pellets of different size |
| BFE 12: | Spherical pellets, some loose powder is observed and there is a tendency of agglomeration |
| BFE 13: | Pellets of different sizes with a tendency of having a rough surface |
| BFE 14: | Like for BFE 13 |
| BFE 15: | Like BFE 13 and 14 |

Conclusion

A. Quality of Calcium Carbonate Employed

Table I shows that different process parameters were employed dependent on the quality used of the calcium carbonate. Different properties of the cores made from the two different qualities were also observed, cf. Table II. The calcium carbonate obtained from Faxe Kalk seems to be superior to the calcium carbonate obtained from Nomeco. This might be due to the fact that the two qualities differ on the following points:

1. Calcium carbonate from Nomeco has a higher true density (2.79) than the calcium carbonate obtained from Faxe Kalk (2.73)
2. The content of an insoluble acidic residue is higher in the calcium carbonate from Faxe Kalk than in the calcium carbonate from Nomeco
3. The Nomeco calcium carbonate seems to have a higher ability of water sorption than the Faxe Kalk calcium carbonate; this fact makes it very difficult to make suspensions of Nomeco calcium carbonate having a concentration above about 30% w/w for use as a feed in the spray drying process
4. The ratio between the true density of the pellets ($D_p$) and the true density of the inert carrier (calcium carbonate) employed ($D_t$) is higher for pellets prepared from the Faxe Kalk calcium carbonate than for pellets prepared from Nomeco calcium carbonate (see Table III below). The true density of the pellets, $D_p$, is a sum of contributions from the inert carrier material, any binding agent used and any residual amount of water. The ratio $D_p/D_t$ is therefore less than 1 and gives an expression for voids or hollow spaces in the pellets into which the inert gas, helium, cannot penetrate. The observation in difference in $D_p/D_t$ for the two different calcium carbonate qualities may therefore imply that pellets prepared from the Nomeco calcium carbonate have a tendency of having hollow spaces within the pellets themselves.

TABLE III

| Batch | Substance | Dp | Dt | Dp/Dt |
|---|---|---|---|---|
| BFE 1 | $CaCO_3$, FAXE | 2,5843 | 2,7311 | 0,95 |
| BFE 2 | $CaCO_3$, FAXE | 2,5468 | — | 0,93 |
| BFE 4 | $CaCO_3$, NOMECO | 2,0880 | 2,7906 | 0,75 |
| BFE 5 | $CaCO_3$, NOMECO | 2,2443 | — | 0,80 |
| BFE 7 | $CaCO_3$, FAXE | 2,5355 | 2,7311 | 0,91 |
| BFE 8 | $CaCO_3$, FAXE | 2,4826 | — | 0,91 |
| BFE 9 | $CaCO_3$, FAXE | 2,5978 | — | 0,95 |
| BFE 10 | $CaSO_4$ | * | * | * |
| BFE 12 | $CaCO_3$, FAXE | 2,5322 | 2,7311 | 0,93 |
| BFE 13 | $CaCO_3$, NOMECO | 2,6160 | 2,7906 | 0,94 |
| BFE 14 | $CaCO_3$, NOMECO | 2,5429 | — | 0,91 |
| BFE 15 | MgO | * | * | * |
| APV | $CaCO_3$, FAXE | 2,5973 | 2,7311 | 0,95 |
| NIRO | $CaCO_3$, FAXE | 2,6006 | 2,7311 | 0,95 |

*not determined due to solvate formation

B. Concentration of Binding Agent

The concentration of the binding agent employed, PVP K30, does not seem to have a significant influence on the quality of the cores (pellets) obtained from the Faxe Kalk calcium carbonate. Neither has the concentration of the binding agent significant influence on the friability of the pellets. However, at a concentration of about 8% w/w based on dry matter there is some tendency to formation of agglomerates, thus for a binding agent of the type PVP K30 it seems as if the optimal concentration is in a range about 3–7% w/w such as 4–6% w/w based dry matter.

Example 2

Preparation of Theophylline Pellets According to the Invention

A suspension was prepared from the following ingredients:

TABLE 2

| Ingredients | kg | % w/w in suspension | % w/w dry matter |
|---|---|---|---|
| Calcium carbonate | 11.4 | 28.2 | 76 |
| PVA (Mowiol, Hoechst) | 0.6 | 1.5 | 4 |
| Theophylline | 3.0 | 7.4 | 20 |
| Distilled water | 25.4 | 62.9 | |

Silicon oil was added as an anti-foaming agent in an amount not exceeding 10 ml.

PVA (polyvinylacetate) (0.6 kg) functioning as a binder is dissolved in warm water (6.0 kg) at a temperature of about 50° C. in a concentration corresponding to 10% w/w dry matter. The remaining amount of water is then added under stirring.

Theophylline (3.0 kg) and calcium carbonate (11.4 kg) are then added to the mixture under stirring and silicon oil is added to suppress formation of foam which otherwise would have created a technical problem for the finished formulation because too many air bobbles in the finished formulation would lead to hollow pellets. The resulting mixture is immediately before use sieved through a 177 μm sieve. The resulting suspension, i.e. the feed, is manually stirred at regular intervals to ensure a homogen feed.

The homogen feed is sprayed into the above-mentioned NIRO P-6.3N spray drying equipment using a pressure nozzle atomizer positioned at the bottom of the chamber and with the spray pointing upwards in order to obtain as large particles as possible. The following process parameters are employed:

| Inlet temperature: | 330° C. |
|---|---|
| Outlet temperature: | 135° C. |
| Fluidising air velocity: | 650 kg/hour |

The resulting theophylline containing cores are a mixture of spherical pellets and non-spherical pellets. Most of the pellets are of spheric form and the non-spherical pellets show a tendency of having a spheric form with narrowings. The pellets show a minor tendency to agglomerate. The mean particle size of the pellets are 119 μm as measured by means of the Malvern System 2600 apparatus and the following results were obtained:

i) about 10% w/w of the particles have a size of less than 44 μm, ii) about 50% w/w of the particles have a size of less than 119 μm, and iii) about 90% w/w of the particles have a size of less than 178 μm.

The tapped density of the calcium carbonate pellets is 0.76 g/ml measured after compaction 100 times and the loss after drying is about 0% w/w.

Conclusion

The use of PVA as binder needs gives acceptable results. However, a tendency of agglomeration of the pellets was observed during spray-drying.

Example 3

Preparation of Theophylline Containing Pellets According to the Invention

A suspension was prepared from the following ingredients:

TABLE 3

| Ingredients | kg | % w/w in suspension | % w/w dry matter |
|---|---|---|---|
| Calcium carbonate | 5.2 | 35.5 | 76 |
| PVP (Povidon, Mecol) | 0.5 | 1.9 | 4 |
| Theophylline | 1.4 | 9.4 | 20 |
| Distilled water | 7.8 | 53.2 | |

Silicon oil was added as an anti-foaming agent in an amount of at the most 10 ml.

PVP (polyvinylpyrrolidone) functioning as a binder is dissolved in warm water at a temperature of about 50° C. in a concentration corresponding to 10% w/w dry matter. The remaining amount of water is then added under stirring. Theophylline and calcium carbonate are then added to the mixture under stirring and silicon oil is added in order to avoid foaming. The resulting mixture is immediately before use sieved through a 177 μm sieve. The resulting suspension, i.e. the feed, is manually stirred at regular intervals to ensure a homogen feed.

The homogen feed is sprayed into the above-mentioned NIRO P-6.3N spray drying equipment using a pressure nozzle atomizer positioned at the bottom of the chamber and with the spray pointing upwards in order to obtain as small particles as possible. The following process parameters are employed:

| Inlet temperature: | 280° C. |
|---|---|
| Outlet temperature: | 153° C. |
| Fluidising air velocity: | 650 kg/hour |

The resulting theophylline containing cores are spherical pellets having a mean particle size of 158 μm as measured by means of the Malvern System 2600 apparatus and the following results were obtained:

i) about 10% w/w of the particles have a size of less than 81 μm, ii) about 50% w/w of the particles have a size of less than 158 μm, and iii) about 90% w/w of the particles have a size of less than 227 μm.

The tapped density of the calcium carbonate pellets is 0.84 g/ml measured after compaction 250 times, and the loss after drying is 1.0% w/w.

The friability was found to be 2.5% after 5 minutes testing and 4.0% after a testing time of 35 minutes.

The flowability expressed as the flow time and the flow angle was found to be 3.90 sec (flow time) and 7.20° (flow angle) (determined as described in method A herein). Using method B described herein, an angle of repose was found to be 19°, i.e. the pellets are freely flowing.

Example 4

Coating of Inert Pellets with an Active Substance

Pellets from Example 1 were coated with two different active substances (chlorpheniramine maleate and hydrocodone bitartrate both supplied by Nomeco, Denmark).

| Composition: | | |
|---|---|---|
| I | Pellets from Example 1 | 500 g |
| II | Chlorpheniramine maleate | 12.3 g |
| III | Purified water | 200 g |
| IV | Hydrocodone bitartrate | 15.4 g |
| V | Purified water | 300 g |

The active substance II is dissolved in the purified water III and the pellets are coated with resulting solution using a fluidized bed apparatus (GPCG I/622 Wurster, Glatt GmbH, Germany) and the following conditions:

| | |
|---|---|
| Nozzle position: | bottom (in order to obtain a long drying time and thereby avoiding agglomeration) |
| Inlet air temperature: | about 60° C. |
| Product temperature: | 27° C.–30° C. |
| Nozzle pressure: | 2 bar |
| Spraying rate: | about 10 g/ml |
| Fluidized air velocity: | 18–28 m$^3$/hour |

Then the active substance IV is dissolved in the purified water V. The pellets coated with the active substance II (as described above) are then coated with the solution of IV in V using the same apparatus as described above and the following conditions:

| | |
|---|---|
| Nozzle position: | bottom (in order to obtain a long drying time and thereby avoiding agglomeration) |
| Inlet air temperature: | about 60° C. |
| Product temperature: | 27° C–33° C. |
| Nozzle pressure: | 1.5 bar |
| Spraying rate: | about 10 g/ml |
| Fluidized air velocity: | 22–34 m$^3$/hour |

The quantitative content of both of the active substances were about 100% w/w when the coated pellets were analysed by a HPLC method using a SPD-6A UV-detector, a C-R 5A integrator and a LC-6A liquid chromatograph, all from Shimadzu, Japan (cf. below). These results are very promising and indicates that it will be possible to apply a further coating (e.g. a modified release coating) on the thus coated pellets without washing off the active substances by the coating process.

| HPLC method: | |
|---|---|
| Column: | Zorbax SCX, 5 μm, 25 cm (No. 54) |
| Mobile phase: | 6.84 g K$_2$HPO$_4$, 3 H$_2$O (from Merck, Germany) + 630 ml water + 370 ml methanol (from Lab Scan, Niels Peter Mark, Denmark), adjusted to a pH of 6.8 by addition of ortho-phosphoric acid (from Merck, Germany) |
| Flow: | 1.8 ml/min |
| Detection: | 220 nm |
| Temperature: | room temperature |
| Injection: | 20 μl |

Example 5

Preparation of a Powder Spray for Application to the Nose

Pellets prepared according to Examples 3 and 4 above were filled into hard gelatine capsules. The addition of a glidant in connection with the filling was not necessary as the spray-dried pellets in themselves have a suiteble flowability. The dose of theophylline may be adjusted by mixing the pellets prepared according to Example 3 with an appropriate amount of a filler such as, e.g., lactose.

The thus prepared capsules are administered to the nose by means of an insulator such as, e.g., the Lomudal® insulator.

Alternatively, capsules may be prepared by filling into hard gelatine capsules spray-dried pellets which are prepared according to Example 1 and subsequently coated with an active drug substance, optionally in combination with a bioadhesive film.

Example 6

Surelease® Coating of Pellets Prepared by Spray-Drying 1 kg of pellets prepared as described in Example 3 above is coated with a Surelease® coating by applying 4 kg of the following coating mixture per kg. pellets. The coating mixture is prepared by diluting Surelease® (which is a 25% w/w dispersion of ethylcellulose in water, cf. information under the heading "Materials") to 12.5% w/w with water.

The coating mixture is applied on the pellets by means of a fluidized bed apparatus (GPCG I/6" Wurster, Glatt GmbH, Germany) using the following conditions:

| | |
|---|---|
| Nozzle position: | bottom (in order to obtain a long drying time and thereby avoiding agglomeration) |
| Inlet air temperature: | 75–80° C. |
| Product temperature: | approx. 28° C. |
| Nozzle pressure: | 3.0–3.5 bar |
| Spraying rate: | 12 g/ml |
| Fluidized air velocity: | 24–28 m$^3$/hour |

The amount of coating mixture employed per kg pellets is based on the following calculation:

| Parameters: | |
|---|---|
| Thickness aimed at: | 10 μm corresponding to 1 mg film/cm$^2$ |
| Mean particle size (diameter): | about 150 μm |
| Bulk density: | about 0.7 g/cm$^3$ |
| Volume of one spheric pellets: | 4/3 πr$^3$ = 1.767 × 10$^{-6}$ cm$^3$ (r = radius) |
| Weight of one pellet (w): | 1.236 × 10$^{-3}$ mg |
| Surface area (SA): | πd$^2$ = 7.065 × 10$^{-4}$ cm$^2$ (d = diameter in cm) |
| Amount of coating mixture to be applied expressed as % dry lacquer substance: | [SA (cm$^2$) × thickness of the film (mg/cm$^2$)/w (mg)] × 100% = about 57% w/w |

In conclusion, in order to obtain a film thickness of about 10 μm, an amount of polymer corresponding to about 57% of the weight of the pellets should be employed.

The surface of the coated pellet is relatively smooth as evidenced by electron microscopy.

In the same manner as described above, coated pellets were prepared by use of various amounts of coating mixture in order to obtain pellets having various amounts of film coating applied (i.e. 2%, 10%, 20%, 30%, 40%, and 50% w/w, respectively). In order to obtain a coating of 50% w/w, 4 kg of Surelease® diluted to 12.5% w/w was employed per kg pellets. The thus coated pellets were subjected to a dissolution test in order to test the release rate of theophylline versus the thickness of the film.

Dissolution test

The coated theophylline pellets were subjected to a dissolution test employing in each of the vessels a dose corresponding to 300 mg of theophylline of the pellets and 900 ml of phosphate buffer solution pH 7.5, USP as dissolution medium.

The following results were obtained (the values given are the mean values of two determinations and the values are given as the weight percentages released after the stated time period):

TABLE 4

| time | % film coating | | | | | |
|---|---|---|---|---|---|---|
| (hours) | 2% | 10% | 20% | 30% | 40% | 50% |
| 0.5 | 94.2 | 81.9 | 36.3 | 12.6 | 8.5 | 9.6 |
| 1.0 | 96.3 | 94 | 57.1 | 20.3 | 13.7 | 13.7 |
| 2.0 | 97.2 | 97.2 | 83.7 | 36.7 | 23.5 | 21.9 |
| 3.0 | 101 | 101 | 97.2 | 51.9 | 35.5 | 31.8 |
| 4.0 | 99.3 | 101 | 101 | 63.7 | 45 | 41.6 |
| 5.0 | | 99.7 | 102 | 76.3 | 56 | 48.6 |
| 6.0 | | 99.8 | 102 | 86.2 | 63.8 | 57.5 |
| 24 | | 99.9 | 104 | 106 | 101 | 98.4 |

Figure 2:
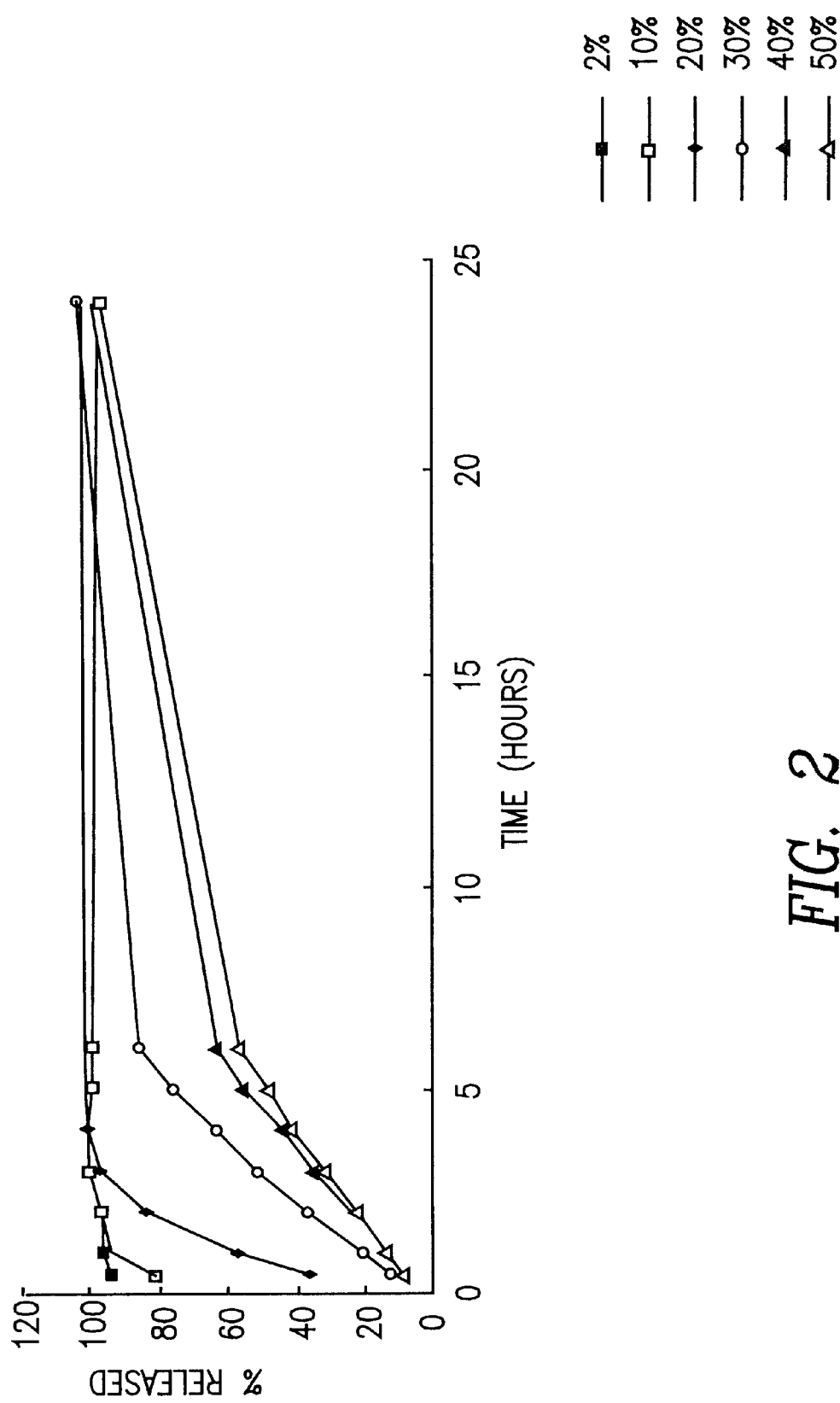
FIG. 2 shows the dissolution profile of theophylline pellets prepared by a spray-drying process and coated with a Su-release®—coating (for further details, see Example 6 herein)

The results given above in Table 4 are also shown in FIG. 2. The results clearly show that the pellets prepared by spray-drying are sufficiently robust to withstand a coating procedure and that a modified release coating can be obtained. Furthermore, the results show that the retardation in release increases as the coating thickness increases. Pellets coated with 2% w/w or 10% w/w Surelease® release almost instantly the total amount of theophylline contained in the pellets.

Example 7

Ethylcellulose Coating of Pellets Prepared by Spray-Drying 1 kg of pellets prepared as described in Example 3 above is coated with a ethylcellulose coating by applying 2.5 kg of the following coating mixture per kg pellets. The coating mixture is prepared by dissolving 10% of ethylcellulose 20 cps in ethanol and adding 8% w/w DBS (dibutylsebacate) as a plasticizer (2500 g coating solution per kg pellets have the following composition:

| | |
|---|---|
| Ethanol | 2250 g |
| Ethocel ® | 250 g |
| Dibuthylsebacate | 20 g | corresponding to 9.9% w/w Ethocel® as dry matter and 0.8% w/w dibuthylsebacetate as dry matter).

The coating solution is applied on the pellets by means of a fluidized bed apparatus (GPCG I/6" Wurster, Glatt GmbH, Germany) using the following conditions:

| | |
|---|---|
| Nozzle position: | bottom (in order to obtain a long drying time and thereby avoiding agglomeration) |
| Inlet air temperature: | 50–65° C. |
| Product temperature: | 28–35° C. |
| Nozzle pressure: | 3.5 bar |
| Spraying rate: | 15 g/ml |
| Fluidized air velocity: | 24 m³/hour |

A film coating having a thickness of about 5 μm is obtained. 2.5 kg coating solution per kg pellets is employed corresponding to 450 g dry matter per kg pellets (45% w/w).

The surface of the coated pellet is relatively smooth (but not as smooth as the pellets which were coated with Surelease®) as evidenced by electron microscopy.

In the same manner as described above, coated pellets were prepared by use of various amounts of coating mixture in order to obtain pellets having various amounts of film coating applied (i.e. 8.6%, 11.9%, 16.2%, 20.5%, 24.8%, and 27% w/w, respectively). The thus coated pellets were subjected to a dissolution test in order to test the release rate of theophylline versus the thickness of the film.

Dissolution test

The coated theophylline pellets were subjected to a dissolution test employing in each of the vessels 1.5 gram (corresponding to 300 mg of theophylline) of the pellets and 900 ml of phosphate buffer solution pH 7.5, USP as dissolution medium.

The following results were obtained (the values given are the mean values of two determinations and the values given are the weight percentages released after the stated time period):

TABLE 5

| time | % film coating | | | | | |
|---|---|---|---|---|---|---|
| (hours) | 8.6% | 11.9% | 16.2% | 20.5% | 24.8% | 27% |
| 0.5 | 34.3 | 34.5 | 7.1 | 3.1 | 2.6 | 1.1 |
| 1.0 | 48.7 | 42.7 | 12.4 | 4.8 | 3.5 | 1.9 |
| 2.0 | 63.7 | 55.4 | 20.1 | 8.8 | 6.8 | 4.3 |
| 3.0 | 73 | 69.2 | 27.2 | 11.7 | 9.3 | 6.4 |
| 4.0 | 76.2 | 70.9 | 29.6 | 12.7 | 10.1 | 7 |
| 5.0 | 79.7 | 73.1 | 33.5 | 14.2 | 11.8 | 8.7 |
| 6.0 | 80.3 | 74.5 | 36.8 | 16.4 | 13.7 | 10.6 |
| 24 | 93.8 | 83.5 | 62.1 | 36.2 | 26 | 21 |

Figure 3:
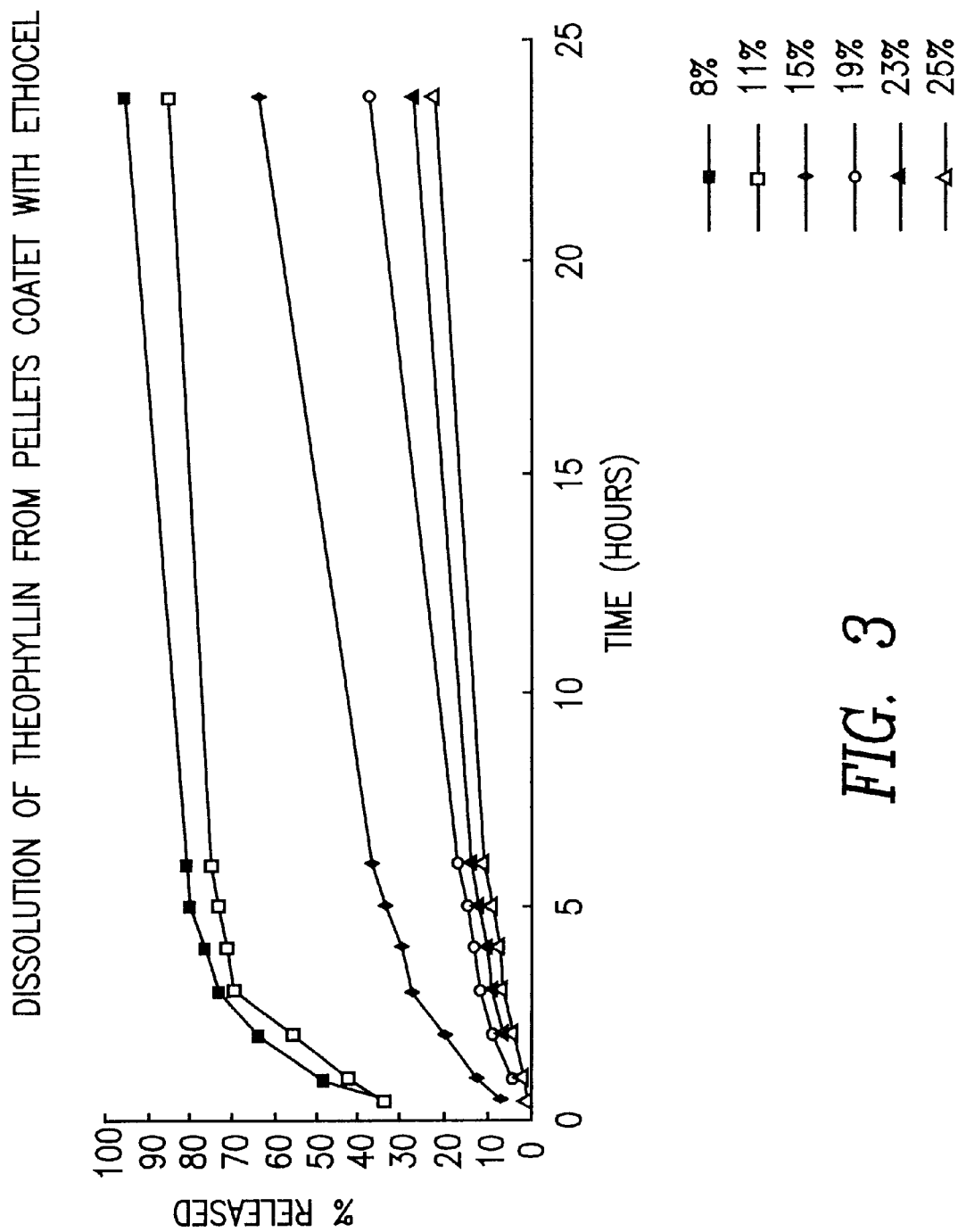
FIG. 3 shows the dissolution profile of theophylline pellets prepared by a spray-drying process and coated with an Etho-cel®—coating (for further details, see Example 7 herein)

The results given above in Table 5 are also shown in FIG. 3. The results clearly show that the pellets prepared by spray-drying are sufficiently robust to withstand a coating procedure and that a modified release coating can be obtained. Furthermore, the results show that the retardation in release increases as the coating thickness increases. Pellets coated with 8.6% w/w or 11.9% w/w ethylcellulose display also a modified release pattern. The results also show that less film is needed when using an ethanol based film than when an aqueous based film is used. This is most likely due to the dissolution characteristics of ethylcellulose in ethanol as ethylcellulose easily dissolves in ethanol and thus perform a more homogeneous application of the film on the pellets. In the case of an aqueous based film, the polymer (i.e. ethylcellulose) is dispersed in the medium as small particles which makes the coating more difficult.

Example 8

Hydrogenated Fat Coating of Pellets Prepared by Spray-Drying 1 kg of pellets prepared as described in Example 3 above is coated with the following coating mixture. A hydrogenated vegetable fat was melted and during the process it was kept at a temperature of about 10° C. above the melting temperature of the fat employed (68° C.). About 400 g of hydrogenated vegetable fat was used per kg pellets.

The coating mixture is applied on the pellets by means of a fluidized bed apparatus (GPCG I/6" Wurster, Glatt GmbH, Germany) using the following conditions:

| Nozzle position: | top (has proved to be the best method for hot-melt coating) |
|---|---|
| Inlet air temperature: | 30–50° C. |
| Product temperature: | 38–44° C. |
| Nozzle pressure: | 3.5 bar |
| Spraying rate: | 20 g/ml |
| Fluidized air velocity: | 24–48 m³/hour |

In the same manner as described above, coated pellets were prepared by use of various amounts of coating mixture in order to obtain pellets having various amounts of film coating applied (i.e. 2%, 16%, and 40% w/w, respectively). The thus coated pellets were subjected to a dissolution test in order to test the release rate of theophylline versus the thickness of the film.

Dissolution test

The coated theophylline pellets were subjected to a dissolution test employing in each of the 6 vessels 1.5 gram (corresponding to 300 mg of theophylline) of the pellets and 900 ml of phosphate buffer solution pH 7.5, USP as dissolution medium.

The following results were obtained (the values given are the mean values of two determinations and the values given are the weight percentages released after the stated time period):

TABLE 6

| time | % film coating | | |
|---|---|---|---|
| (hours) | 2% | 16% | 40% |
| 0.5 | 16.3 | 0.5 | 1.3 |
| 1.0 | 25 | 1.3 | 2 |
| 2.0 | 32.7 | 2.3 | 3.4 |
| 3.0 | 38.1 | 3.6 | 6.3 |
| 4.0 | 39.5 | 4.4 | 6.6 |
| 5.0 | 42.5 | 5.7 | 7.7 |
| 6.0 | 45.2 | 7.2 | 8.2 |
| 24 | 64.1 | 13.1 | 22.2 |
| 48 | 80.7 | 20.4 | 30.7 |

Figure 4:
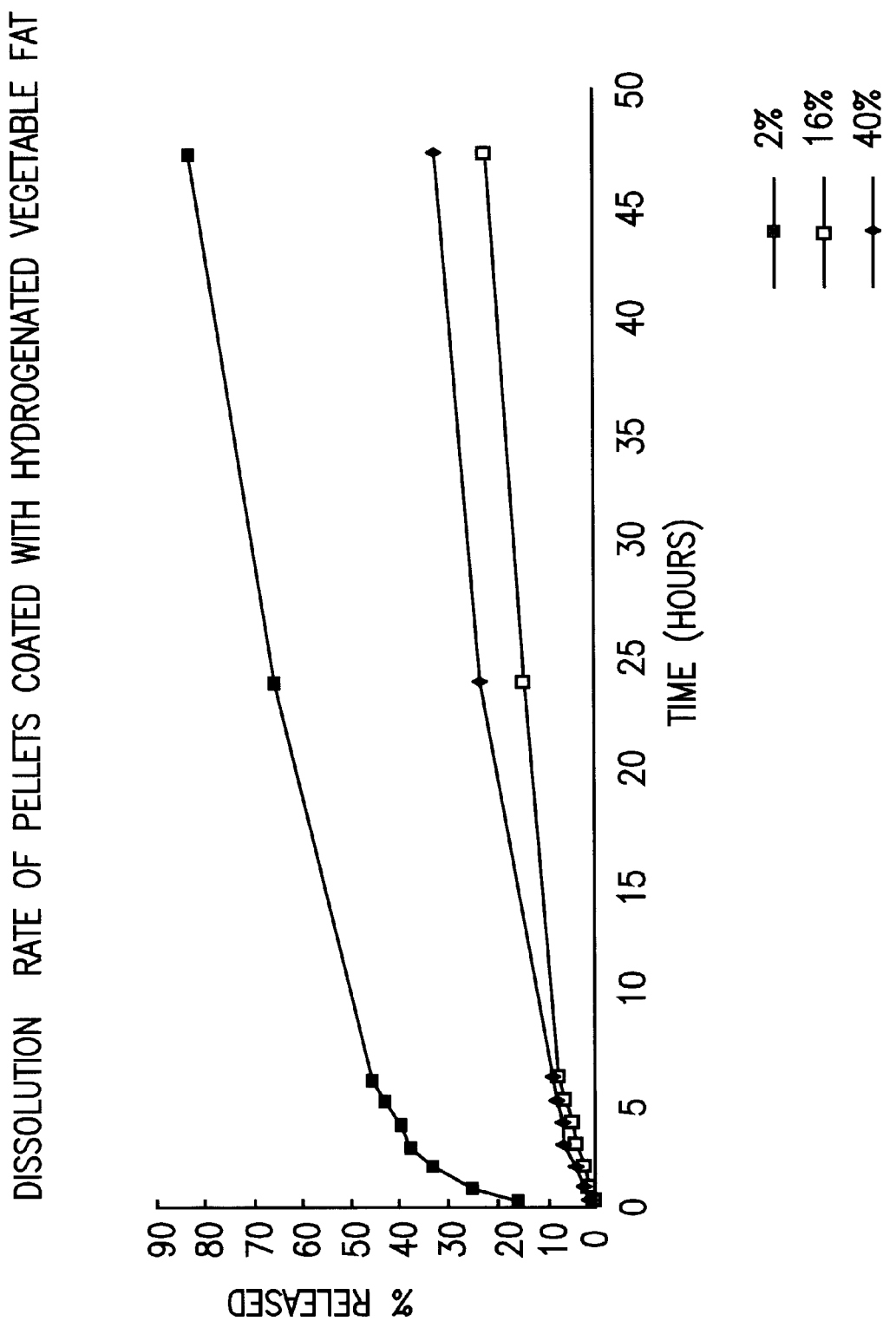
FIG. 4 shows the dissolution profile of theophylline pellets prepared by a spray-drying process and coated with a hydro-genated fat-coating (for further details, see Example 8 herein)

The results given above in Table 6 are also shown in FIG. 4. The results clearly show that the pellets prepared by spray-drying are sufficiently robust to withstand a coating procedure and that a modified release coating can be obtained. The results with respect to a coating with 2% w/w show that the dissolution was only retarded to a minor degree. However, the results with respect to coating with 16% w/w or 40% w/w show a more pronounced retardation.

Example 9
Glyceryl Monooleate Coating of Pellets Prepared by Spray-Drying 1 kg of pellets prepared as described in Example 1 above is coated with a glyceryl monooleate (GMO) coating by applying a coating mixture containing 80% w/w glyceryl monooleate in an amount corresponding to 300 g GMO per kg pellets. The coating mixture is prepared by melting the GMO prior to the addition of ethanol and the solution is kept at a slightly elevated temperature of about 45° C.

The coating mixture is applied on the pellets by means of a fluidized bed apparatus (GPCG I/6" Wurster, Glatt GmbH, Germany) using the following conditions:

| Nozzle position: | bottom |
|---|---|
| Inlet air temperature: | about 15° C. |
| Product temperature: | 17–21° C. |
| Nozzle pressure: | 1.5 bar |
| Spraying rate: | 7 g/ml |
| Fluidized air velocity: | approx. 30 m³/hour |

The coated pellets were tested for bioadhesiveness in the test system described herein. The amount applied was 55 mg of pellets. A residual amount of about 72% w/w glyceryl monooleate was found after testing in 30 minutes.

Example 10
Eudragit® Coating of Pellets Prepared by Spray-Drying 0.5 kg of pellets prepared as described in Example 3 above is coated with 1.217 kg of the following coating mixture containing Eudragit® RS 30D as a 30% w/w dispersion in water:

| Eudragit ® RS 30D (30% w/w dispersion) (corresponding to 142.5 g dry matter) | 475.0 g |
|---|---|
| Triethyl citrate (Eudraflex ®) | 28.5 g |
| Microtalcum | 71.3 g |
| Antifoam M 10 | 3.0 g |
| Purified water | 640.0 g |

The coating mixture is applied on the pellets by means of a fluidized bed apparatus (GPCG I/6" Wurster, Glatt GmbH, Germany) using the following conditions:

| Nozzle position: | bottom (in order to obtain a long drying time) |
|---|---|
| Nozzle size | 0.8 mm |
| Inlet air temperature: | 60° C.–75° C. |
| Product temperature: | 25° C.–34° C. |
| Nozzle pressure: | 2 bar |
| Spraying rate: | up to 9 g/ml |
| Fluidized air velocity: | up to 34 m³/hour |

A film coating having a thickness of about 10 µm is obtained. About 43% w/w dry matter is applied on the pellets.

The thus coated pellets were subjected to a dissolution test in order to test the release rate of theophylline versus time.

Dissolution test

The coated theophylline pellets were subjected to a dissolution test employing in each of the vessels a dose corresponding to 300 mg of theophylline of the pellets and 900 ml of 0.1 N hydrochloric acid as dissolution medium. After 2 hours the pH of the dissolution medium was adjusted to pH 6.8 by addition of $Na_3PO_4$.

The following results were obtained (the values given are the mean values of two determinations and the values given are weight percentages released after the stated time period):

| time (hours) | % film coating 43% |
|---|---|
| 0.5 | 6.1 |
| 1.0 | 9.8 |
| 2.0 | 13.8 |
| 3.0 | 16.0 |
| 4.0 | 17.1 |
| 5.0 | 18.3 |
| 6.0 | 18.3 |
| 24 | 29.8 |

Example 11
Preparation of Tablets

Tablets were prepared by direct compression using the coated pellets prepared as described in Example 6 herein (the pellets employed were coated with 50% w/w ethylcellulose film using a Surelease® coating dispersion).

In order to optimize the composition of the tablets, a 4 factor test design was employed testing the following factors at two levels (low and high):
A. Concentration of pellets within the tablets
B. Compression pressure
C. Tablet weight
D. Type of filler/binder The compositions tested were based on the following composition:

| | | |
|---|---|---|
| I | Pellets from Example 6 herein | 20% w/w or 40% w/w |
| II | Microcrystalline cellulose (sieve 710 μm) (Avicel® 101 or 102) | 60% w/w or 80% w/w |
| III | Sodium carboxyrnethylcellulose (sieve 300 μm) | 0.80% w/w |
| IV | Magnesium stearate (sieve 300 μm) | 0.5% w/w |

The tablets were prepared by as follows:

II is sieved and mixed with I. III and IV are mixed and sieved. Finally I+II are mixed with III+IV and tablets are pressed by direct compression using 10 mm flat punches.

The test compositions were prepared by adjusting the amount of pellets and microcrystalline carboxymethylcellulose according to the table showing the test design. The concentrations of the non-tested ingredients in the tablets were the same in all test. The variation in the concentration of ingredients in the tablets and in the compression pressure applied lead to tablets of different weight and different height.

The following test design was employed:

TABLE 8

| No., factor* | A %0 pellets | B compr. pressure** | C tablet weight (mg) | D Avicel® PH |
|---|---|---|---|---|
| BEK 2, (1) | 20 | low | 300 | 101 |
| BEK 4, a | 40 | low | 300 | 101 |
| BEK 3, b | 20 | high | 300 | 101 |
| BEK 5, ab | 40 | high | 300 | 101 |
| BEK 9, c | 20 | low | 500 | 101 |
| BEK 11, ac | 40 | low | 500 | 101 |
| BEK 10, bc | 20 | high | 500 | 101 |
| BEK 12, abc | 40 | high | 500 | 101 |
| BEK 6, d | 20 | low | 300 | 102 |
| BEK 13, ad | 40 | low | 300 | 102 |
| BEK 8, bd | 20 | high | 300 | 102 |
| BEK 14, abd | 40 | high | 300 | 102 |
| BEK 15, cd | 20 | low | 500 | 102 |
| BEK 17, acd | 40 | low | 500 | 102 |
| BEK 16, bcd | 20 | high | 500 | 102 |
| BEK 18, abcd | 40 | high | 500 | 102 |

*: (1) is a tablet wherein all the factors tested are at the low level, the letters "a, b, c, and/or d" indicate that factor A, B, C, and/or D are tested at the high level
**: In the tables given below, the compression pressure is expressed by means of the crushing strength of the tablets prepared The tablets prepared were subjected to two test, namely i) a dissolution test using 0.1 N hydrochloric acid as dissolution medium for the first 2 hours and then changing the pH of the dissolution medium by means of addition of $Na_3PO_4$, and ii) a test for crushing strength (for further details see under the heading "Apparatus and methods").

Figure 5:
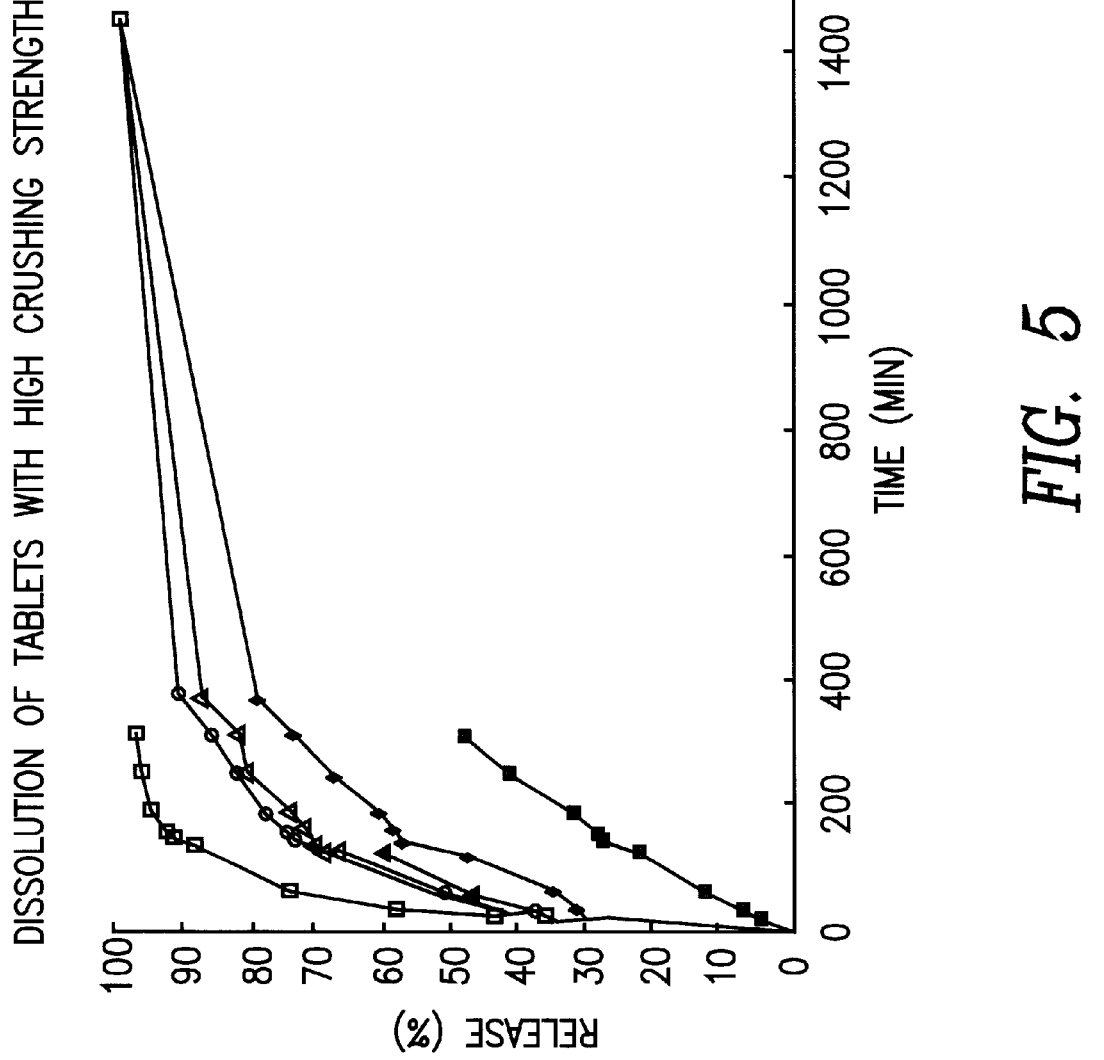
FIG. 5 shows the dissolution profile of theophylline multiple unit tablets prepared by compression of coated pellets with a compression pressure corresponding to a high crushing strength (for further details, see Example 11 herein)
Figure 6:
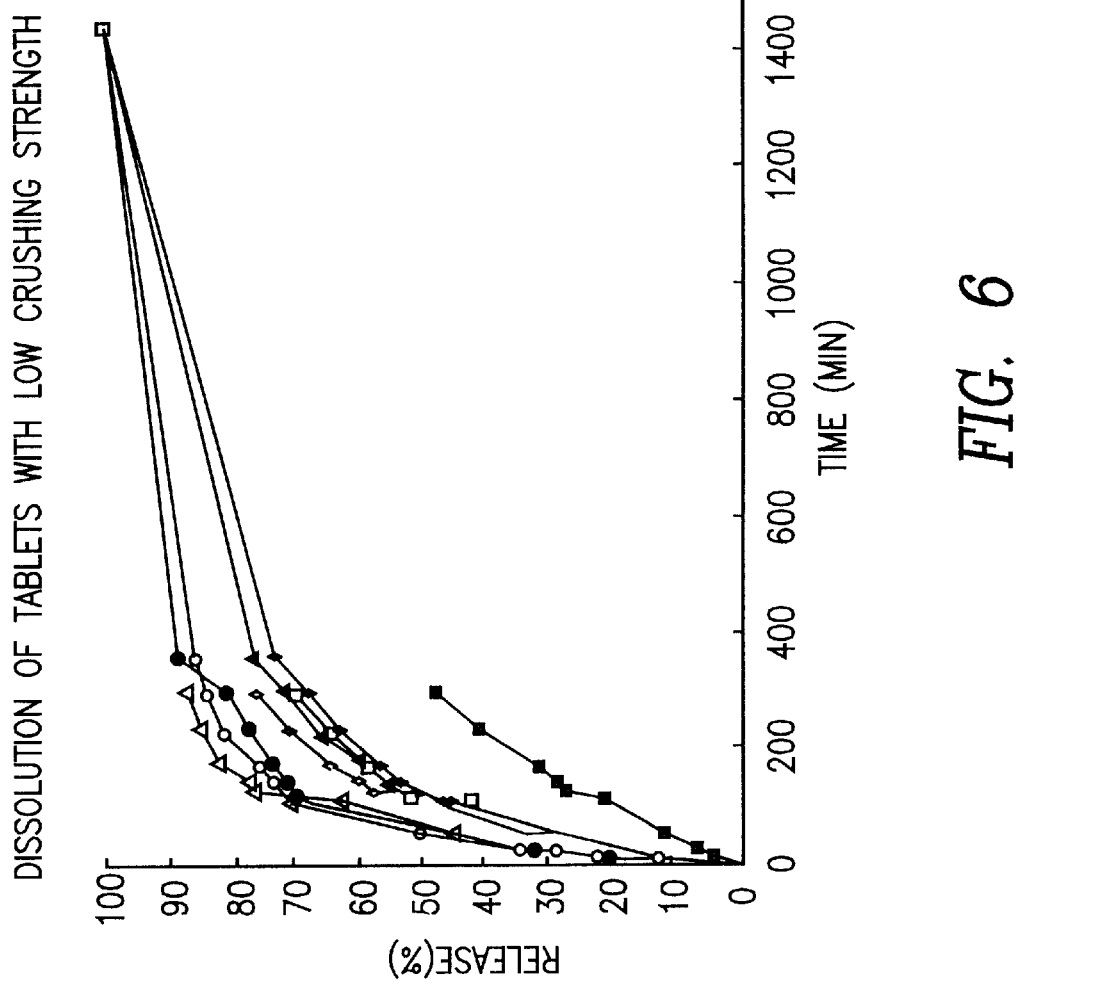
FIG. 6 shows the dissolution profile of theophylline multiple unit tablets prepared by compression of coated pellets with a compression pressure corresponding to a low crushing strength (for further details, see Example 11 herein)
Figure 7:
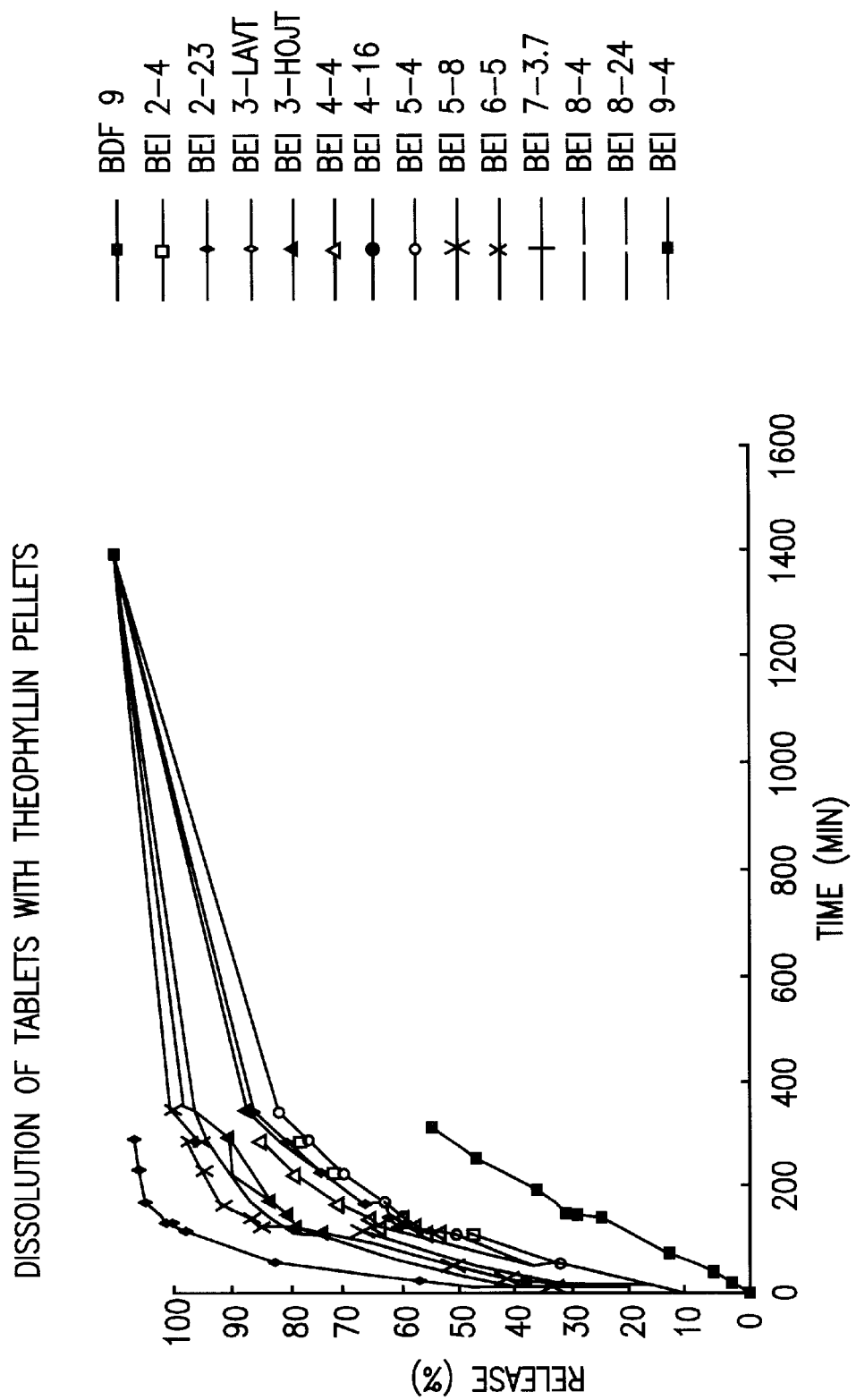
FIG. 7 shows the dissolution profile of theophylline multiple unit tablets prepared by compression of coated pellets (for further details, see Example 11 herein)

The dissolution test results are shown in FIGS. 5–7 and in Table 9 below (the values given are the mean values of two determinations and are given as the weight percentages released after the stated time period) in which the crushing strengths also are indicated. Formulation BDF 9 is the pellets from Example 6 herein which are employed in the preparation of the tablets.

TABLE 9

| Dissolution time (min) | Formulation (crushing strength, kp) | | | | |
|---|---|---|---|---|---|
| | BDF 9 | BEK 2 (3.3) | BEK 3 (23.4) | BEK 9 (3.5) | BEK 10 (20.0) |
| 0 | 0 | 0 | 0 | 0 | 0 |
| 15 | 4.05 | 12.80 | 44.13 | 12.29 | 30.71 |
| 30 | 6.67 | 18.89 | 58.96 | 19.52 | 32.98 |
| 60 | 11.51 | 30.80 | 75.67 | 31.03 | 36.96 |
| 120 | 20.69 | 44.24 | 90.14 | 48.22 | 50.90 |
| 135 | 26.12 | 53.97 | 93.52 | 55.95 | 60.41 |
| 150 | 27.43 | 56.44 | 94.58 | 57.31 | 62.19 |
| 180 | 30.63 | 60.62 | 96.84 | 60.65 | 64.88 |
| 240 | 39.41 | 67.32 | 98.40 | 67.33 | 71.38 |
| 300 | 45.99 | 72.84 | 99.11 | 72.48 | 78.20 |
| 360 | | | | 77.94 | 84.15 |
| 1440 | 95.73 | 103.0 | 102.24 | 105.68 | 106.45 |
| | BEK 4 (4.2) | BEK 5 (16.9) | BEK 11 (4.6) | BEK 12 (18.3) | BEK 6 (4.5) |
| 0 | 0 | 0 | 0 | 0 | 0 |
| 15 | 12.18 | 27.87 | 11.34 | 31.17 | 21.00 |
| 30 | 19.77 | 39.24 | 19.54 | 38.72 | 32.02 |
| 60 | 33.91 | 54.52 | 20.74 | 47.82 | 50.50 |
| 120 | 50.73 | 70.81 | 48.87 | 61.42 | 59.66 |
| 135 | 58.71 | 77.87 | 56.00 | | 85.23 |
| 150 | 60.59 | 79.46 | 57.53 | | 86.20 |
| 180 | 65.65 | 83.00 | 61.18 | | 91.38 |
| 240 | 72.16 | 87.03 | 67.93 | 83.82 | 94.29 |
| 300 | 77.69 | 91.22 | 73.36 | 88.16 | 96.87 |
| 360 | | | 78.67 | 92.26 | |
| 1440 | 101.1 | 106.1 | 101.8 | 101.9 | 109.8 |
| | BEK 8 (17.8) | BEK 13 (3.7) | BEK 14 (15.9) | BEK 15 (3.5) | BEK 16 (19.8) |
| 0 | 0 | 0 | 0 | 0 | 0 |
| 15 | 57.46 | 23.60 | 45.49 | 21.54 | 34.17 |
| 30 | 66.39 | 34.72 | 57.99 | 33.05 | 42.79 |
| 60 | 75.9 | 48.93 | 70.81 | 48.94 | 53.75 |
| 120 | 87.21 | 67.73 | 84.27 | 69.94 | 69.36 |
| 135 | | 77.07 | | 72.33 | 70.97 |
| 150 | | 79.26 | | 73.87 | 72.38 |
| 180 | | 80.21 | | 76.52 | 75.06 |
| 240 | | 86.05 | | 80.00 | 81.65 |
| 300 | | 90.43 | | 83.55 | 83.55 |
| 360 | | 94.49 | | 91.05 | 88.13 |
| 1440 | | 106.5 | | 102.6 | 100.7 |
| | BEK 17 (3.7) | BEK 18 (21.0) | | | |
| 0 | 0 | 0 | | | |
| 15 | 22.73 | 46.83 | | | |
| 30 | 35.10 | 60.51 | | | |
| 60 | 51.32 | 72.24 | | | |
| 120 | 71.72 | 83.78 | | | |
| 135 | 73.15 | | | | |
| 150 | 74.30 | | | | |
| 180 | 77.31 | | | | |
| 240 | 82.76 | | | | |
| 300 | 85.41 | | | | |
| 360 | 87.23 | | | | |
| 1440 | 100.6 | | | | |

The results from the dissolution tests show the tablets containing Avicel® PH 101 have dissolution profiles which are more suitable for modified release than the dissolution profiles relating to tablets containing Avicel® PH 102 (the dissolution was faster when Avicel® PH 102 was used indicating that the degree of rupture of the film membrane was higher for the Avicel® PH 102 containing tablets than for the Avicel® PH 101 containing tablets). Dissolution profile for the pellets before compression is also given in FIGS. 5–7 (formulation BDF 9) and it is seen that compression in all cases lead to a faster release indicating that the compression has some impact on the release rate most likely due to a minor (but reproducible rupture of the film membrane during compression).

The results show that with respect to the concentration of the pellets (20% w/w and 40% w/w, respectively), no difference in dissolution rate is observed for the tablets BEK 2 and BEK 4 compressed with low compression strength; the percentage dissolved remains the same, i.e. the degree of rupture of the film membrane on the pellets caused by the compression is substantially the same independent on the compression pressure (expressed as the crushing strength of the resulting tablets). The same pattern is observed for BEK 9 and BEK 11 which have a high tablet weight, thus indicating that the tablet weight is without significant influence on the dissolution profile. In general, the dissolution rate of the tablets is faster than the dissolution rate for the pellets and, furthermore, there is a tendency towards a decrease in the dissolution rate when the compression pressure decreases.

The best tablet composition of the tested one seems to be the composition in which Avicel® PH 101 is employed and where the compression pressure was low.

Example 12

Preparation of Tablets with Pellets Coated with Eudragit® RS 30D

Tablets were prepared by direct compression using the coated pellets prepared as described in Example 10 herein (the pellets employed were coated with 43% w/w Eudragit® RS 30D film).

| | Composition: | |
|---|---|---|
| | | mg/tablet |
| I | Pellets from Example 10 | 100 |
| II | Avicel PH 101 | 394 |
| III | Sodium carboxymethylcellulose | 3.75 |
| IV | Magnesium stearate | 2.50 |

II is sieved (710 μm) and mixed with I. III and IV are mixed and sieved (300 μm). I+II are mixed with III+IV. The tablets are pressed by direct compression using 12 mm flat punches. Two batches are prepared, one applying a compression pressure corresponding to a crushing strength of 5.5 kp and the other batch is prepared by applying a compression pressure corresponding to a crushing strength of 19.0 kp.

The tablets prepared are subjected to two tests, namely a dissolution test using 0.1 N hydrochloric acid for the first 2 hours and then changing the pH of the dissolution medium to a pH of 6.8 by addition of $Na_3PO_4$ and a test for crushing strength.

TABLE 10

| Dissolution time (min) | Formulation (crushing strength, kp) | | |
|---|---|---|---|
| | BDF 48* | BEL 12 (5.5) | BEL 12 (19) |
| 30 | 6.1 | 10.1 | 10.2 |
| 60 | 9.8 | 14.3 | 13.3 |
| 120 | 13.8 | 17.6 | 17.1 |
| 180 | 16.0 | 20.1 | 19.9 |
| 240 | 17.1 | 21.6 | 21.2 |
| 300 | 18.3 | 22.7 | 22.9 |
| 360 | 18.3 | 23.5 | 23.8 |
| 1440 | 29.8 | 36.1 | 34.7 |

*: BDF 48 is the pellets before compression

The results from the dissolution tests show that the coating applied is very flexible and the release characteristics of the film are maintained even after compression at two different compression pressures. This result is very important because it indicates that the coated cores according to the invention easily may be compressed into tablets without any essential rupture of the film membrane on the coated cores. The small increase in dissolution time observed with respect to the two tablet formulations compared with the pellet formulation indicates a minor but reproducible degree of rupture of the film membrane on the coated cores. The tablets prepared with different compression pressure have almost the same dissolution profile which also supports that the film applied on the cores is very flexible and stable.

Example 13
Preparation of Effervescent Tablets

Tablets having the following composition were prepared:

| | mg/tablet |
|---|---|
| Pellets from Example 6 coated with 50% w/w ethylcellulose | 219 |
| Sorbitol | 439.5 |
| Citric acid | 439.5 |
| Sodium hydrogencarbonate | 330.0 |
| Polyethylene glycol 6000 | 72.0 |

A flat punch having a diameter of 13 mm was used and the tablets were prepared by means of direct compression using a DIAF TM 20 tabletting machine. Two batches were prepared, one applying a compression pressure corresponding to a crushing strength of 4.3 kp and the other batch was prepared by applying a compression pressure corresponding to a crushing strength of 12.3 kp (denoted BEL 1 low and BEL 1 high, respectively).

Figure 8:
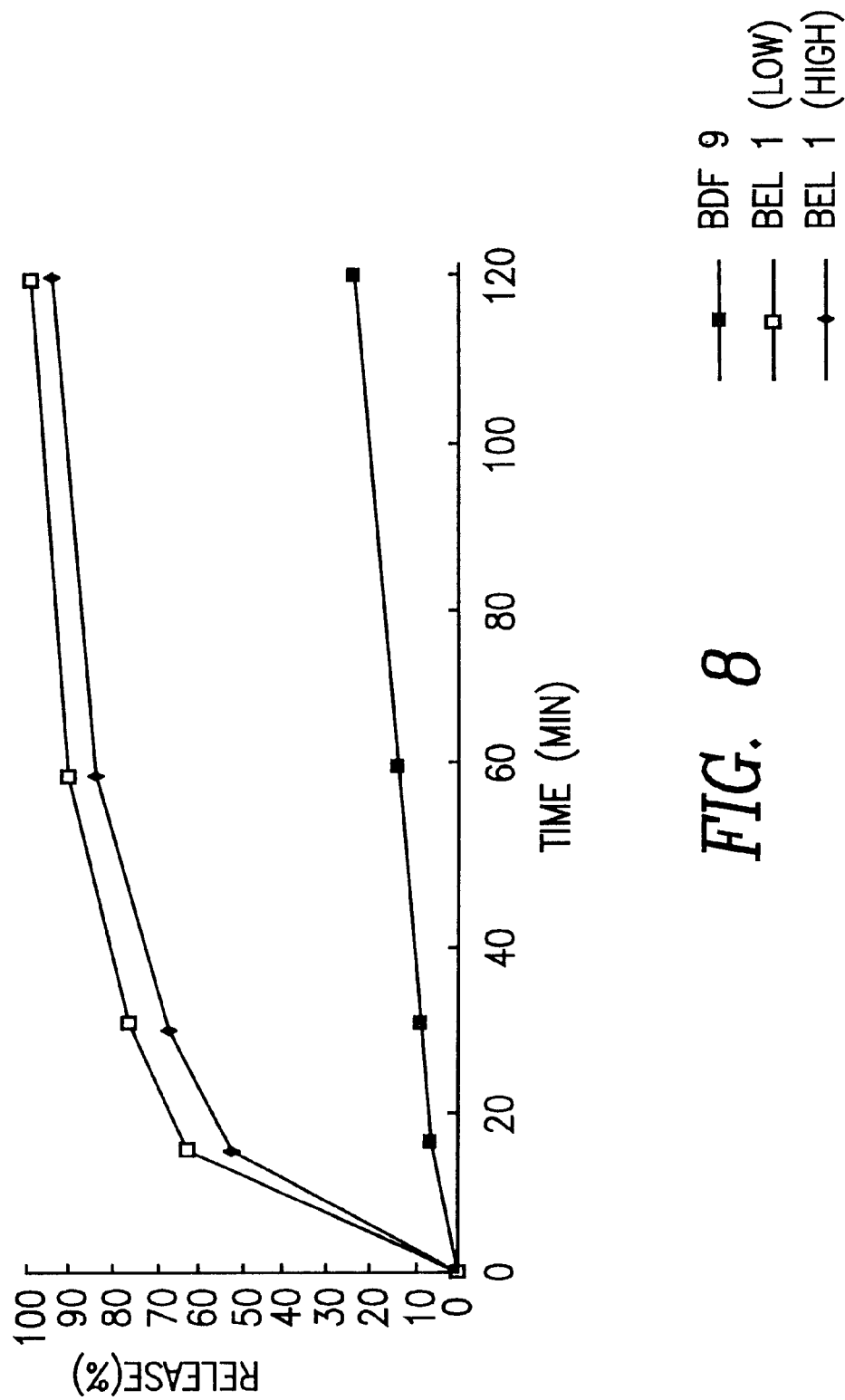
FIG. 8 shows the dissolution profile of effervescent tablets prepared by compression of coated pellets (for further details, see Example 13 herein)

The dissolution of the tablets prepared was tested and compared with the dissolution of the pellets employed (denoted BDF 9). The results are shown below (the values given are the weight percentages released after the stated time period) and in FIG. 8.

TABLE 11

| Dissolution time (min) | Formulation | | |
|---|---|---|---|
| | BDF 9 | BEL 1, low | BEL 1, high |
| 0 | 0 | 0 | 0 |
| 15 | 4.23 | 62.6 | 52.7 |

TABLE 11-continued

| Dissolution time (min) | Formulation | | |
|---|---|---|---|
| | BDF 9 | BEL 1, low | BEL 1, high |
| 30 | 6.95 | 76.2 | 67.9 |
| 60 | 12.03 | 90.3 | 84.1 |
| 120 | 21.61 | 98.6 | 93.8 |

The tablets disintegrated within 2 minutes and generally, the dissolution rate of the tablets was faster than for tablets prepared as described in Example 11 which probably is caused by a partial rupture of the coated pellets during compression. The results show that the effervescent tablet formulation is acceptable but still needs some optimization.

Example 14

Preparation of a Dispersion of Modified Release Pellets

Pellets from Examples 6, 7, or 8 are suspended in a liquid medium (e.g. a liquid medium as described below). The concentration of pellets in the mixture should preferably not be too high in order to avoid a gritty mouth feel upon oral intake. Correspondingly, the mean particle size should not be more too large, i.e. preferably not larger than 250 μm.

An example of a liquid medium:

| Avicel RC 591 | about 1–3% w/w such as, e.g., 2.6% w/w |
|---|---|
| Xanthan gum | about 0–1.5% w/w such as, e.g., 0.075% w/w |
| Instant sugar | about 5–10% w/w such as, e.g., 7.5% w/w |
| Pellets | about 5–20% w/w |
| purified water | up to 100% w/w |

All ingredients except the purified water are mixed and filled into a suitable container, such as, e.g., a bottle, or alternatively, an accurately amount of the mixture is filled into sachets. Immediately before use, the thus obtained reconstitutable mixture is mixture with purified water and the resulting suspension is stirred.

In accordance with the above, a mixture was prepared with the following composition:

| Avicel ® RC 591 | 1.85% w/v |
|---|---|
| Instant sugar | 7.50% w/v |
| Pellets from Example 6 | 30.0% w/v |
| Methylparahydroxybenzoat | 0.1% w/v |
| Distilled water | up to 100% w/v |

The formulation was left at room temperature without stirring and at appropriate intervals, the formulation was tested with respect to viscosity, pH, sedimentation, and release of theophylline. The following results were obtained:

TABLE 12

| | time (days) | | | | | |
|---|---|---|---|---|---|---|
| | 1 | 2 | 4 | 7 | 9 | 14 |
| Viscosity, mPs | 74 | 73 | 68 | 69 | 72 | 70 |
| Tixotropi | + | + | + | + | + | + |
| pH | 6.90 | 6.99 | 7.05 | 7.00 | 7.04 | 6.94 |
| Sedimentation: | | | | | | |
| $V_s/V_0 \times 100\%$ | 100 | | 95 | | 97 | 98 |
| revolutions | 1 | | 2 | | 2 | 1 |
| % w/w release | | | | 34% | | 36% |

The viscosity below 100 mPas seems to be of choice in order to ensure that the formulation easily can be poured from a bottle. The sedimentation and the redispersibility are acceptable but should be optimized.

Example 15

Comparison of the Flowability of Inert Cores for Use According to the Invention and Zinc-Bacitracin Particles According to Danish Patent Application No. 4402/77

The following experiment was performed in order to investigate any difference between the flowability of zinc-bacitracin particles containing calcium carbonate as described in Danish Patent Application No. 4402/77 and the flowability of cores according to the present invention. The flow angle for the various compostions listed in Table IV below was determined using method A described herein. Batch BFE 21 was a product (ALBac) from A.L., Norway, and batches BFE 7–10 are described in Example 1C herein.

The following results were obtained:

TABLE IV

| Batch No. | Diameter of Disc outlet (mm) | Flow angle° |
|---|---|---|
| Cores according to Example 1A | 6 | * |
| | 9 | 5.27 |
| | 12 | 0.46 |
| Cores according to Example 1B | 6 | 12.46 |
| | 9 | 4.30 |
| | 12 | 0.38 |
| BFE 21 (ZnBackalk) | 6 | — |
| | 9 | 33.25 |
| | 12 | 12.26 |
| BFE 7 FAXE 6% | 6 | 13.8 |
| | 9 | 4.27 |
| | 12 | 0.5 |
| BFE 8 FAXE 8% | 6 | 16.2 |
| | 9 | 5.6 |
| | 12 | 0.55 |
| BFE 9 FAXE 4 | 6 | 13.5 |
| | 9 | 5.2 |
| | 12 | 0.5 |
| BFE 10 CaSO$_4$ 4% | 6 | 15.3 |
| | 9 | 5.9 |
| | 12 | 1.3 |

—Not measurable
*Not measured

From Table IV it can be seen that the flowability of cores according to the invention is markedly better as the zinc-bacitracin particles from A.L.

We claim:

1. A pharmaceutical multiple unit particulate formulation comprising individual units in the form of coated cores, wherein at least 50% w/w of the cores before coating have a particle size within a range of about 90–225 μm, when tested as described herein, each coated core comprising
   i) a pharmaceutically acceptable inert carrier which is present in the core in a first concentration of at least about 20% w/w calculated on the total weight of the core, and which is selected from the group consisting of calcium carbonate, calcium silicate, calcium magnesium silicate, calcium phosphate, kaolin, sodium hydrogen carbonate, sodium sulfate, barium carbonate, barium sulfate, magnesium sulfate, magnesium carbonate, and activated carbon, and ii) an active drug substance being present in a layer on the outer surface of the cores, the pharmaceutically acceptable inert carrier being such a material which—when formulated into uncoated cores containing the pharmaceutically acceptable inert carrier optionally in combination with a binder and with a second concentration of the inert carrier of at least 80% w/w calculated on the total weight of the uncoated core—has a friability (weight loss in % w/w) of at the most about 20%, when tested as described herein, and the cores have a flow angle—when tested according to method A described herein using a diameter of the disc outlet of 9 mm—of at the most 30°.

2. A pharmaceutical particulate formulation according to claim 1, wherein the second concentration of the pharmaceutically acceptable inert carrier in said uncoated cores containing the inert carrier optionally in combination with a binder is at least 85% w/w, calculated on the total weight of the uncoated core.

3. A pharmaceutical particulate formulation according to claim 1, wherein said uncoated cores containing the inert carrier optionally in combination with a binder have a friability (weight loss in % w/w) of at the most about 15%, when tested as described herein.

4. A pharmaceutical particulate formulation according to claim 1, wherein the first concentration of the inert carriers is at least about 50% w/w.

5. A pharmaceutical particulate formulation according to claim 4, wherein at least 50% w/w of the cores before coating have a particle size within a range of about 90–225 µm, when tested as described herein.

6. A pharmaceutical particulate formulation according to claim 1, wherein at least 70% w/w of the cores before coating have a particle size within the range of about 90–225 µm, when tested as described herein.

7. A pharmaceutical particulate formulation according to claim 1, wherein at least 50% w/w of the cores before coating have a particle size of at the most 180 µm, when tested as described herein.

8. A pharmaceutical particulate formulation according to claim 1, wherein the pharmaceutically acceptable inert carrier and the active substance are in admixture.

9. A pharmaceutical particulate formulation according to claim 1, wherein the coating on the cores is selected from the group consisting of modified release coatings, film coatings, bioadhesive coatings, and sugar coatings.

10. A pharmaceutical particulate formulation according to claim, 1, wherein the inert carrier is calcium carbonate.

11. A pharmaceutical particulate formulation according to claim, 1, further comprising a pharmaceutically acceptable excipient.

12. A pharmaceutical particulate formulation according to claim 11 wherein the pharmaceutically acceptable excipient is selected from the group consisting of fillers, binders, disintegrants, glidants, and lubricants.

13. A pharmaceutical formulation according to claim 1, adapted for oral, buccal, mucosal, nasal, rectal, topical, or wound administration.

14. A solid dosage form comprising a pharmaceutical particulate formulation according to claim 13.

15. A solid dosage form according to claim 14 in unit dosage form.

16. A solid dosage form according to claim 14, wherein the unit dosage form is selected from the group consisting of tablets, capsules, effervescent tablets, chewable tablets, lozenges, immediate release tablets, modified release tablets, suppositories, vagitories, implants, and plasters.

17. A solid dosage form according to claim 14 adapted for oral, buccal, mucosal, nasal, rectal, vaginal, or topical administration, or administration to wounds.

18. A solid dosage form according to claim 14 which is coated with a coating selected from the group consisting of a film coating, a sugar coating, a bioadhesive coating, and a modified release coating.

19. A pharmaceutical multiple unit particulate formulation comprising individual units in the form of coated cores, wherein at least 50% w/w or the cores before coating have a particle size within a range of about 90–225 µm, when tested as described herein, each coated core comprising i) a pharmaceutically acceptable inert carrier which is present in the core in a first concentration of at least about 20% w/w calculated on the total weight of the core, and which is selected from the group consisting of calcium carbonate, calcium silicate, calcium magnesium silicate, calcium phosphate, kaolin, sodium hydrogen carbonate, sodium sulfate, barium carbonate, barium sulfate, magnesium sulfate, magnesium carbonate, and activated carbon, and ii) an active drug substance, the pharmaceutically acceptable inert carrier being such a material which—when formulated into uncoated cores containing the pharmaceutically acceptable inert carrier optionally in combination with a binder and with a second concentration of the inert carrier of at least 80% w/w calculated on the total weight of the uncoated core—has a friability (weight loss in % w/w) of at the most about 20%, when tested as described herein, and the cores have a flow angle—when tested according to method A described herein using a diameter of the disc outlet of 9 mm—of at the most 30°, and the coating of the coated cores comprising a first and a second layer, the first layer comprising the active drug substance.

20. A pharmaceutical multiple unit particulate formulation comprising individual units in the form of coated cores, wherein at least 50% w/w of the cores before coating have a particle size of at the most 250 µm, when tested as described herein, each coated core comprising i) a pharmaceutically acceptable inert carrier which is present in the core in a first concentration of at least about 20% w/w calculated on the total weight of the core, and which is selected from the group consisting of calcium carbonate, calcium silicate, calcium magnesium silicate, calcium phosphate, kaolin, sodium sulfate, barium carbonate, barium sulfate, magnesium sulfate, magnesium carbonate, and activated carbon, and ii) an active drug substance,
the pharmaceutically acceptable inert carrier being such a material which—when formulated into uncoated cores containing the pharmaceutically acceptable inert carrier optionally in combination with a binder and with a second concentration of the inert carrier of at least 80% w/w calculated on the total weight of the uncoated core—has a friability (weight loss in % w/w) of at the most about 20%, when tested as described herein, and the cores have a flow angle—when tested according to method A described herein using a diameter of the disc outlet of 9 mm—of at the most 30°, and the coating of the coated cores comprising a first and a second layer, the second layer comprising the active drug substance.

\* \* \* \* \*

UNITED STATES PATENT AND TRADEMARK OFFICE
CERTIFICATE OF CORRECTION

PATENT NO. : 5,958,458
DATED : September 28, 1999
INVENTOR(S) : Tomas Norling, Lone Norgaard Jensen and Jens Hansen It is certified that error appears in the above-identified patent and that said Letters Patent is hereby corrected as shown below:

Column 39,
Lines 22, 28, 33, 36, 40, 44, 48, 51, 55, 57 and 60, after the word "pharmaceutical", insert -- multiple unit --;
Line 34, cancel "carriers", insert -- carrier --;

Column 40,
Lines 1 and 4, after the word "pharmaceutical", insert -- multiple unit --; and
Line 60, after the word "kaolin", insert -- sodium hydrogen carbonate --.

Signed and Sealed this

Second Day of July, 2002

Attest:

Attesting Officer

JAMES E. ROGAN
Director of the United States Patent and Trademark Office